(12) United States Patent
Doyle

(10) Patent No.: US 7,662,969 B2
(45) Date of Patent: Feb. 16, 2010

(54) EFFICIENT AZIRIDINATION OF OLEFINS CATALYZED BY DIRHODIUM CATALYSTS

(75) Inventor: Michael P. Doyle, Glenn Dale, MD (US)

(73) Assignee: University of Maryland, College Park, College Park, MD (US)

( * ) Notice: Subject to any disclaimer, the term of this patent is extended or adjusted under 35 U.S.C. 154(b) by 414 days.

(21) Appl. No.: 11/375,020

(22) Filed: Mar. 15, 2006

(65) Prior Publication Data

US 2006/0211870 A1 Sep. 21, 2006

Related U.S. Application Data

(60) Provisional application No. 60/662,679, filed on Mar. 17, 2005.

(51) Int. Cl.
C07D 275/06 (2006.01)
C07D 203/26 (2006.01)
C07D 403/02 (2006.01)
(52) U.S. Cl. .................. 548/207; 548/954; 548/962
(58) Field of Classification Search .............. 548/207, 548/954, 962
See application file for complete search history.

(56) References Cited

U.S. PATENT DOCUMENTS

| | | | |
|---|---|---|---|
| 4,026,709 A | 5/1977 | Piller et al. | |
| 4,840,890 A | 6/1989 | Kamei et al. | |
| 5,703,246 A | 12/1997 | Aggarwal et al. | |
| 5,712,331 A | 1/1998 | Ryang | |
| 5,929,252 A | 7/1999 | Sharpless et al. | |
| 5,936,127 A | 8/1999 | Zhang | |
| 6,258,960 B1 | 7/2001 | Antilla et al. | |
| 6,307,087 B1 | 10/2001 | Buchwald et al. | |
| 6,395,916 B1 | 5/2002 | Buchwald et al. | |
| 6,946,560 B2 | 9/2005 | Buchwald et al. | |

OTHER PUBLICATIONS

Guthikonda, Kiran. A Unique and Highly Efficient Method for Catalytic Olefin Aziridination. Journal of the American Chemical Society. 124 (2002) 13672-13673.*
Ali, S. I. et al., "Pyridinium Hydrobromide Perbromide: A Versatile Catalyst for Aziridination of Olefins Using Chloramine-T," *Org. Lett.* 1999 1(5); 705-707.
Anada, M. et al., "A New Dirhodium(Ii) Carboxamidate Complex As A Chiral Lewis Acid Catalyst for Enantioselective Hetero-Diels-Alder Reactions," *Angew. Chem., Int. Ed.*, 2004 43:2665.
Angeles-Boza, A.M. et al., "DNA Binding and Photocleavage in Vitro by New Dirhodium(II) dppz Complexes: Correlation to Cytotoxicity and Photocytotoxicity," *Inorg. Chem.* 2004 43:8510-8519.
Berry, J.F. et al., "A Hardwon Dirhodium Paddlewheel With Guanidinate Type (Hpp) Bridging Ligands," *Dalton Trans.* 2005 7; (23):3713-3715.
Bode, J.W . et al., "Intramolecular Regioselective Insertion into Unactivated Prochiral Carbon-Hydrogen Bonds with Diazoacetates Catalyzed by Chiral Dirhodium(II) Carboxamidates. Highly Enantioselective Total Synthesis of Natural Lignan Lactones," *J. Org. Chem.* 1996 61:9146-9155.
Catino, A.J. et al., "Dirhodium(II) Caprolactamate: An Exceptional Catalyst for Allylic Oxidation," *J. Am. Chem. Soc.* 2004 126(42):13622-13623.
Catino, A.J. et al., "Efficient Aziridination Of Olefins Catalyzed By Mixed-Valent Dirhodium(II,III) Caprolactamate," *Org. Lett.* 2005 7(13):2787-2790.
Chifotides, H.T. et al., "Interactions of Metal-Metal-Bonded Antitumor Active Complexes with DNA Fragments and DNA," *Acc. Chem. Res.* 2005 38:146-156.
Cotton, F.A. et al., "The First Dirhodium Tetracarboxylate Molecule Without Axial Ligation: New Insight Into The Electronic Structures Of Molecules With Importance In Catalysis And Other Reactions," *J. Am. Chem. Soc.* 2002 124(20):5658-5660.
Cui, Y. et al., "Efficient Aziridination Of Olefins Catalyzed By A Unique Disilver(I) Compound," *J. Am. Chem. Soc.* 2003 125(52):16202-16203.
Dauban, P. et al., "Synthesis of Cyclic Sulfonamides via Intramolecular Copper-Catalyzed Reaction of Unsaturated Iminoiodinanes," *Org. Lett.* 2000 2(15):2327-2329.
Dauban, P. et al., "Copper-Catalyzed Nitrogen Transfer Mediated By Iodosylbenzene PHI=O," *J. Am. Chem. Soc.* 2001 123:7707-7708.
Dauban, P. et al., "Intramolecular Bromine-Catalyzed Aziridination: A New Direct Access To Cyclic Sulfonamides," *Tetrahedron Lett.* 2001 42:1037-1040.
Dauban, P. et al., "Iminoiodanes and C-N Bond Formation in Organic Synthesis," *Synlett* 2003:1571.
Dequeant ,M.Q. et al., "Dirhenium Paddlewheel Compounds Supported by N,N'-Dialkylbenzamidinates: Synthesis, Structures, and Photophysical Properties," *Inorg. Chem.* 2004 43:7887-7892.
Doyle, M. P. et al., "The Influence of Ligands on Dirhodium(II) on Reactivity and Selectivity in Metal Carbene Reactions," *Prog. Inorg. Chem.* 2001 49:113-168.
Doyle, M.P., "Asymmetric syntheses with catalytic enantioselective metal carbene transformations," *Russ. Chem. Bull.* 1994 43: 1770-1782.
Doyle, M.P., "Enantiomer Differentiation in Intramolecular Carbon-Hydrogen Insertion Reactions of Racemic Secondary Alkyl Diazoacetates Catalyzed by Chiral Dirhodium(II) Carboxamidates," *Russ. Chem. Bull.* 1995 44:1729-1734.

(Continued)

*Primary Examiner*—Kamal A Saeed
*Assistant Examiner*—Samantha L Shterengarts
(74) *Attorney, Agent, or Firm*—Jeffrey I. Auerbach; Edell, Shapiro & Finnan, LLC

(57) ABSTRACT

This invention relates to compositions and methods for achieving the efficient aziridination of organic molecules, especially olefins. More specifically, the invention is directed to a mild, selective, and efficient aziridination protocol that involves catalysis by a mixed-valent dirhodium(II,III) catalyst ($Rh_2^{5+}$). Especially preferred sources for forming such mixed-valent dirhodium(II,III) catalyst ($Rh_2^{5+}$) are dirhodium(II) carboxamidates, such as dirhodium(II) caprolactamate, and their derivatives and analogues.

10 Claims, 3 Drawing Sheets

OTHER PUBLICATIONS

Doyle, M.P. et al., "Dirhodium(II) Tetrakis(Carboxamidates) with Chiral Ligands. Structure and Selectivity in Catalytic Metal Carbene Transformations," *J Am. Chem. Soc.* 1993 115:9968-9978.

Doyle, M.P. et al., "Electronic And Steric Control In Carbon-Hydrogen Insertion Reactions Of Diazoacetoacetates Catalyzed By Dirhodium(II) Carboxylates And Carboxamides," *J. Am. Chem. Soc.* 1993 115(3):958-964.

Doyle, M.P. et al., "Enhancement of Enantiocontrol/Diastereocontrol in Catalytic Intramolecular Cyclopropanation and Carbon-Hydrogen Insertion Reactions of Diazoacetates with Rh2(4S-MPPIM)4" *Tetrahedron Lett.* 1995 36:7579-7582.

Doyle, M.P. et al., "Highly Enantioselective Route to β-Lactams via Intramolecular C-H Insertion Reactions of Diazoacetylazacycloalkanes Catalyzed by Chiral Dirhodium(II) Carboxamidates," *Synlett* 1995 1075-1076.

Doyle, M.P. et al., "Optimization of Enantiocontrol for Carbon-Hydrogen Insertion with Chiral Dirhodium(II) Carboxarnidates. Synthesis of Natural Dibenzylbutyrolactone Lignans from 3-Aryl-1-propyl Diazoacetates in High Optical Purity," *J. Org. Chem.* 1995 60:6654-6655.

Doyle, M.P. et al., "Chiral Dirhodium Carboxamidates. Catalysts for Highly Enantioselective Syntheses of Lactones and Lactams," *Aldrichimica Acta* 1996 29(1):3-11.

Doyle, M.P. et al., "Highly Enantioselective Intramolecular Cyclopropanation Reactions of N-Allylic-N-methyldiazoacetamides Catalyzed by Chiral Dirhodium(II) Carboxamidates," *J. Org. Chem.* 1996 61:2179-2184.

Doyle, M.P. et al., "Highly Enantioselective Oxonium Ylide Formation and Stevens Rearrangement Catalyzed by Chiral Dirhodium(II) Carboxamidates," *Tetrahedron Lett.* 1997 38:4367-4370.

Doyle, M.P. et al., "Enantiocontrol in the Generation and Diastereoselective Reactions of Oxonium Ylides Catalyzed by Chiral Dirhodium(II) Carboxamidates. Metal-Stabilized Ylides as Reaction Intermediates," *J. Am. Chem. Soc.* 1998 120:7653-7654.

Doyle, M.P. et al., "Recent Advances in Asymmetric Catalytic Metal Carbene Transformations," *Chem. Rev.* 1998 98:911-935.

Doyle, M.P. et al., "Dirhodium(II) Tetrakis[methyl 2-oxaazetidine-4-carboxylate]: A Chiral Dirhodium(II) Carboxamidate of Exceptional Reactivity and Selectivity," *Organic Lett.* 2000 2:1145-1147.

Doyle, M.P. et al., "Optimization of Enantiocontrol in cis-Selective Cyclopropanation Reactions Catalyzed by Dirhodium(II) Tetrakis-[alkyl 2-oxaazetidine-4(S)-carboxylates]," *J. Chem. Soc. Chem. Commun.* 2000 867-868.

Doyle, M.P. et al., "A New Class of Chiral Lewis Acid Catalysts for Highly Enantioselective Hetero-Diels-Alder Reactions: Exceptionally High Turnover Numbers from Dirhodiurn(II) Carboxamidates," *J. Am. Chem. Soc.* 2001 123:5366-5367.

Doyle, M.P. et al., "Epoxides and aziridines from diazoacetates via ylide intermediates," *Org. Lett.* 2001 3(6):933-935.

Doyle, M.P. et al., "High Selectivity from Configurational Match/Mismatch in Carbon-Hydrogen Insertion Reactions of Steroidal Diazoacetates Catalyzed by Chiral Dirhodium(II) Carboxamidates," *J. Org. Chem.* 2001 66:8112-8119.

Doyle, M.P. et al., "Reactivity Enhancement for Chiral Dirhodium(II) Tetrakis (Carboxamidates)," *Adv. Synth. Cat.* 2001 343(1):112-117.

Doyle, M.P. et al., "Enantioselective Carbon-Hydrogen Insertion is an Effective and Efficient Methodology for the Synthesis of (R)-(−)-Baclofen," *Chirality* 2002 14:169-172.

Doyle, M.P. et al., "Highly Selective Synthesis of a 2-Deoxyxylolcatam via Enantioselective Carbon-Hydrogen Insertion Reactions Using Chiral Dirhodium(II) Carboxamidates," *Adv. Synth. Cat.* 2002 344:91-95.

Doyle, M.P. et al., "Preparation and Catalytic Properties of Immobilized Chiral Dirhodium(II) Carboxamidates," *Organometallics* 2002 21:1747-1749.

Doyle M.P. et al., "Total Synthesis of (S)-(+)-Imperanene. Effective use of Regio- and Enantioselective Intramolecular Carbon-Hydrogen Insertion Reactions Catalyzed by Chiral Dirhodium(II) Carboxamidates," *J. Org. Chem.* 2002 67:2954-2959.

Doyle, M.P. et al., "Asymmetric Catalysis Special Feature Part I: Asymmetric Hetero-Diels-Alder Reaction Catalyzed By Dirhodium(II) Carboxamidates," *Proc. Natl. Acad. Sci.* 2004 101:5391-5395.

Duran, F. et al., "Intramolecular PHI=O Mediated Copper-Catalyzed Aziridination Of Unsaturated Sulfamates: A New Direct Access To Polysubstituted Amines From Simple Homoallylic Alcohols," *Org. Lett.* 2002 4(15):2481-2483.

Espino et al., "Synthesis of 1,3-Difunctionalized Amine Derivatives through Selective C-H Bond Oxidation," *J. Am. Chem. Soc.* 2001 123(28):6935-6936.

Evans, D.A. et al., "Development of the Copper-Catalyzed Olefin Aziridination Reaction," *J. Am. Chem. Soc.* 1994 116:2742-2753.

Forslund, R.E. et al., "Chiral Dirhodium(II) Carboxamidate-Catalyzed [2+2]-Cycloaddition of TMS-Ketene and Ethyl Glyoxylate," *Adv. Synth. Catal.* 2005 347:87-92.

Fruit, C. et al., "Asymmetric Transfer Of Nitrenes Catalyzed By Chiral Dirhodium(II) Using Aromatic Sulfamate Esters," *Tetrahedron-Asymmetry* 2004 15:1019.

Gao, G.Y. et al., "Cobalt-Catalyzed Efficient Aziridination Of Alkenes," *Org Lett.* 2005 7(15):3191-3193.

Gillespie, K.M. et al., "Enantioselective Aziridination Using Copper Complexes Of Biaryl Schiff Bases," *J. Org. Chem.* 2002 67(10):3450-4588.

Gullick, J. et al., "Observation Of The Enhancement In Enantioselectivity With Conversion For The Aziridination Of Styrene Using Copper Bis(Oxazoline) Complexes," *Chem. Commun. (Camb)* 2003 (22):2808-2809.

Guthikonda, K. et al., "A Unique and Highly Efficient Method for Catalytic Olefin Aziridination," *J. Am. Chem. Soc.* 2002 124:13672.

Hilt, G., "Direct Electrochemical Aziridination Of Alkenes Under Metal-Free Conditions," *Angew Chem Int Ed. Engl.* 2002 41(19):3586-3588, 3513.

Hu, X. E., "Nucleophilic Ring Opening Of Aziridines," *Tetrahedron* 2004 60:2701.

Jain, S.L. et al., "An Efficient Transition Metal-Free Aziridination Of Alkenes With Chloramine-T Using Aqueous $H_2O_2$/HBr," *Tetrahedron Lett.* 2004 45:8731-8732.

Jeong, J.U. et al., "Bromine-Catalyzed Aziridination of Olefins. A Rare Example of Atom-Transfer Redox Catalysis by a Main Group Element," *J. Am. Chem. Soc.* 1998, 120(27): 6844-6845.

Levites-Agababa, E. et al., "Amidoglycosylation via Metal-Catalyzed Internal Nitrogen Atom Delivery," *Org. Lett.* 2002 4(5):863-865.

Li, Z. et al., "Asymmetric Alkene Aziridination With Readily Available Chiral Diimine-Based Catalysts," *J. Am. Chem. Soc.* 1993 115:5326-5327.

Liang, J.-L. et al., "Metalloporphyrin-Mediated Asymmetric Nitrogen-Atom Transfer To Hydrocarbons: Aziridination Of Alkenes And Amidation Of Saturated C-H Bonds Catalyzed By Chiral Ruthenium And Manganese Porphyrins," *Chem. Eur. J.* 2002 8:1563.

Liang, J.L. et al., "Rhodium(II,II) Dimer As An Efficient Catalyst For Aziridination Of Sulfonamides And Amidation Of Steroids," *Org. Lett.* 2002 4(25):4507-4510.

Liang, J.L. et al., "Chiral Rhodium(II,II) Dimers Catalyzed Enantioselective Intramolecular Aziridination Of Sulfonamides And Carbamates," *Tetrahedron Lett.* 2003 44:5917.

Lutterman, D.A., "Photoinduced One-Electron Reduction of Alkyl Halides by Dirhodium(II,II) Tetraformamidinates and a Related Complex with Visible Light," *Inorg. Chem.* 2005 44:5388-5396.

Mahoney, J.M. et al., "Brønsted Acid-Promoted Olefin Aziridination and Formal Anti-Aminohydroxylation," *J. Am. Chem. Soc.* 2005 127:1354-1355.

Man, W.L. et al. (2004) "Direct Aziridination Of Alkenes By A Cationic (Salen)Ruthenium(VI) Nitrido Complex," *J. Am. Chem. Soc.* 126(47):15336-15337.

Mohr, F. et al., "A practical, fast, and high-yielding aziridination procedure using simple Cu(II) complexes containing N-donor pyridine-based ligands," *J. Org. Chem.* 2005 70(12):4833-4839.

Müller, P. et al., "A Method For Rhodium(II)-Catalyzed Aziridination Of Olefins," *Tetrahedron* 1996 52:1543.

Müller, P., In: Jacobsen E.N. et al., "Transition Metal-Catalyzed Nitrene Transfer: Aziridination And Insertion," *Advances in Catalytic Processes* 1997 2:113; Doyle, M.P., Ed; JAI Press Inc, Greenwich.

Müller, P. et al., "The Rhodium(II)-Catalyzed Aziridination Of Olefins With \{[(4-Nitrophenyl)Sulfonyl]Imino\}Phenyl- Bold Lambda 3-Iodane," *Can. J. Chem.* 1998 76:738-750.

Müller, P. et al., "Enantioselective Catalytic Aziridinations and Asymmetric Nitrene Insertions Into CH Bonds," *Chem. Rev.* 2003 103(8); 2905-2920.

Omura, K. et al., "Design Of A Robust Ru(Salen) Complex: Aziridination With Improved Turnover Number Using N-Arylsulfonyl Azides As Precursors," *Chem. Commun. (Camb)* 2004 21(18):2060-2061.

Padwa, A. et al., "Stereochemical Aspects Of The Iodine(III)-Mediated Aziridination Reaction Of Some Cyclic Allylic Carbamates," *Org. Lett.* 2002 4(13):2137-2139.

Padwa, A. et al., "Rhodium(II)-Catalyzed Aziridination Of Allyl-Substituted Sulfonamides And Carbamates," *J. Org. Chem.* 2004 69(19):6377-6386.

Ren, T., "Substituent Effects in Dinuclear Paddlewheel Compounds: Electrochemical and Spectroscopic Investigations," *Coord. Chem. Rev.* 1998 175:43-58.

Roos, G.H.P. et al., "Synthesis, Structure, and Reactivity of a Novel Series of Diastereomeric Dirhodium(II) TetraCarboxamidates. Catalysts for Asymmetric Diazoacetate Transformations," *Aust. J. Chem.* 1998 51:1-8.

Sanders, C.J. et al., "Structural Origins of a Dramatic Variation in Catalyst Efficiency in Enantioselective Alkene Aziridination: Implications for Design of Ligands Based on Chiral Biaryldiamines," *J. Am. Chem. Soc.* 2000 122:7132-7133.

Siu, T. et al., "Practical Olefin Aziridination With A Broad Substrate Scope," *J. Am. Chem. Soc.* 2002 124:530-531.

Sorasaenee, K. et al., "Isolation of the Novel Dirhodium(II/II) Thiolate Compound $Rh2(\eta^1-C_6H_5S)_2(\mu-C_6H_5S)_2(bpy)_2$," 2003 42(3):661-663.

Takazaki, Y. et al., "A Honeycomb Network Of A Paddlewheel-Type Dirhodium Complex In Two Oxidation States And Pinning Of The Oxidation States," *Chem. Lett.* 2003 32(2):120.

Thakur, V.V. et al., "N-Bromoamides As Versatile Catalysts For Aziridination Of Olefins Using Chloramine-T," *Tetrahedron Lett.* 2003 44:989-992.

Thakur, V.V. et al., "Transition Metal-Catalyzed Regio- and Stereoselective Aminobromination of Olefins with TsNH2 and NBS as Nitrogen and Bromine Sources," *Org. Lett.* 2003 5(6):861-864.

Valenzuela, M. et al., "Influence of the Diene in the Hetero-Diels-Alder Reaction Catalyzed by Dirhodium(II) Carboxamidates," *Synlett* 2004 13:2422.

Yang, X.F. etal., "Stereocontrolled Aziridination Of Imines Via A Sulfonium Ylide Route And A Mechanistic Study," *J. Org Chem.* 2002 67(23):8097-8103.

\* cited by examiner

EFFICIENT AZIRIDINATION OF OLEFINS CATALYZED BY DIRHODIUM CATALYSTS

CROSS-REFERENCE TO RELATED APPLICATIONS

This application claims priority from U.S. Patent Application Ser. No. 60/662,679 (filed Mar. 17, 2005), which application is herein incorporated by reference in its entirety.

USE OF GOVERNMENT FUNDS

This invention was made with government support under NIH RO1GM046503 and NSF CHE0340989 awarded by the National Institutes of Health and the National Science Foundation, respectively. The government has certain rights in the invention.

FIELD OF THE INVENTION

This invention relates to compositions and methods for achieving the efficient aziridination of organic molecules, especially olefins. More specifically, the invention is directed to a mild, selective, and efficient aziridination protocol that involves catalysis by a mixed-valent dirhodium(II,III) catalyst ($Rh_2^{5+}$). Especially preferred sources for forming such mixed-valent dirhodium(II,III) catalyst ($Rh_2^{5+}$) are dirhodium(II,II) carboxamidates, such as dirhodium(II,II) caprolactamate, and their derivatives and analogues.

BACKGROUND OF THE INVENTION

Aziridines are organic compounds having a 3-member ring with a large distortion. The general formula of an aziridine moiety is shown below:

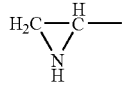

The incorporation of an aziridine into an organic compound is referred to as aziridination. Aziridination is a powerful approach for introducing nitrogen into organic compounds, especially olefins (Müller, P. et al. (2003) "ENANTIOSELECTIVE CATALYTIC AZIRIDINATIONS AND ASYMMETRIC NITRENE INSERTIONS INTO CH BONDS," Chem. Rev. 103(8); 2905-2920; Dauban, P. et al. (2003) "IMINOIODANES AND C—N BOND FORMATION IN ORGANIC SYNTHESIS," Synlett 2003:1571; Jacobsen, E. N. (1999) "FUTURE PERSPECTIVES IN ASYMMETRIC CATALYSIS," 2:607, In: *Comprehensive Asymmetric Catalysis*; Jacobsen, E. N. et al. Eds., Springer-Verlag, Berlin; Müller, P. (1997) "TRANSITION METAL-CATALYZED NITRENE TRANSFER: AZIRIDINATION AND INSERTION," 2:113, In: *Advances in Catalytic Processes*; Doyle, M. P., Ed; JAI Press Inc, Greenwich). Largely regarded for their synthetic versatility, aziridines are well suited for ring opening with an assortment of nucleophiles to yield functionalized amines (Hu, X. E. (2004) "NUCLEOPHILIC RING OPENING OF AZIRIDINES," Tetrahedron 60:2701).

Several methods for directly forming aziridines have been advanced. U.S. Pat. No. 4,840,890 (Kamei et al.), for example, teaches that such compounds can be produced through the intramolecular dehydration of an alkanolamine. U.S. Pat. No. 5,929,252 (Sharpless et al.) discloses that phenyltrimethylammonium tribromide may be employed as a general catalyst for the direct aziridination of olefins. U.S. Pat. No. 5,703,246 (Aggarwal et al.) teaches forming aziridines by reacting a metallocarbon with an alkyl, aryl or heteroaromatic sulfide and then reacting the product with an amide, carbonyl, or olefin. Ylides have been used to catalyze aziridination (Doyle, M. P. et al. (2001) "Epoxides and aziridines from diazoacetates via ylide intermediates," Org. Lett. 3(6):933-935; Yang, X. F. et al. (2002) "STEREOCONTROLLED AZIRIDINATION OF IMINES VIA A SULFONIUM YLIDE ROUTE AND A MECHANISTIC STUDY," J. Org. Chem. 67(23):8097-8103). Electrochemical approaches to aziridination have been proposed (Hilt, G. (2002) "DIRECT ELECTROCHEMICAL AZIRIDINATION OF ALKENES UNDER METAL-FREE CONDITIONS," Angew Chem Int. Ed. Engl. 41(19):3586-3588, 3513). Iodine (III) has been used to mediate aziridination (Padwa, A. et al. (2002)"STEREOCHEMICAL ASPECTS OF THE IODINE(III)-MEDIATED AZIRIDINATION REACTION OF SOME CYCLIC ALLYLIC CARBAMATES," Org. Lett. 4(13):2137-2139). Mahoney, J. M. et al. (2005) disclose the use of Brønsted Acids to catalyze aziridination (BRØNSTED ACID-PROMOTED OLEFIN AZIRIDINATION AND FORMAL ANTI-AMINOHYDROXYLATION," J. Am. Chem. Soc. 127:1354-1355). U.S. Pat. No. 6,258,960 (Antilla et al.) teaches the synthesis of chiral cis-aziridines by reacting an imine with a diazo compound in the presence of a chiral vaulted biary-Lewis Acid complex. U.S. Pat. No. 6,307,087 (Buchwald et al.), U.S. Pat. No. 6,395,916 Buchwald et al.) and U.S. Pat. No. 6,946,560 (Buchwald et al.) disclose $Ar—Ar^1$ compounds, where Ar and $Ar^1$ are optionally substituted monocyclic and polycyclic aromatic and heteroaromatic moieties, and the compounds are produced through the use of a transition metal (including rhodium) and a ligand that may contain an aziridine moiety.

Methods of using aziridines are disclosed in U.S. Pat. No. 5,936,127 (Zhang). U.S. Pat. No. 4,026,709 (Piller et al.) discloses uses of aziridines in facilitating the synthesis of photographic color couplers. U.S. Pat. No. 5,712,331 (Ryang) teaches the use of poly N-substituted aziridines to form curable resins. U.S. Pat. No. 5,936,127 (Zhang) teaches the aziridination of aldehydes as a means for producing chiral heterocyclic compounds.

Despite their value and utility, available methods for the direct preparation of aziridines remain limited. Transition metal catalyzed processes in conjunction with an appropriate nitrene precursor (e.g., iminophenyliodinanes such as TsN=IPh, or in situ variants) have received considerable attention, and represent the best currently available technology for forming aziridine derivatives (Dauban, P. et al. (2001) "COPPER-CATALYZED NITROGEN TRANSFER MEDIATED BY IODOSYLBENZENE PHI=O," J. Am. Chem. Soc. 123:7707-7708; Duran, F. et al. (2002) "INTRAMOLECULAR PHI=O MEDIATED COPPER-CATALYZED AZIRIDINATION OF UNSATURATED SULFAMATES: A NEW DIRECT ACCESS TO POLYSUBSTITUTED AMINES FROM SIMPLE HOMOALLYLIC ALCOHOLS," Org. Lett. 4:2481-4283; Gillespie, K. M. et al. (2002) "ENANTIOSELECTIVE AZIRIDINATION USING COPPER COMPLEXES OF BIARYL SCHIFF BASES," J. Org. Chem. 67(10): 3450-4588; Siu T. et al. (2002) "PRACTICAL OLEFIN AZIRIDINATION WITH A BROAD SUBSTRATE SCOPE," J. Am. Chem. Soc. 124: 530-531; Li, Z. et al. (1993) "ASYMMETRIC ALKENE AZIRIDINATION WITH READILY AVAILABLE CHIRAL DIIMINE-BASED zCATALYSTS," J. Am. Chem. Soc. 115:5326-5327; Evans, D. A. et al. (1994) "DEVELOPMENT OF THE COPPER-CATALYZED OLEFIN AZIRIDINATION REACTION,"‘J. Am. Chem. Soc. 116:2742-2753; Sanders, C. J. et al. (2000) "STRUCTURAL ORIGINS OF A DRAMATIC VARIATION IN CATALYST EFFICIENCY IN ENANTIOSELECTIVE ALKENE AZIRIDINATION: IMPLICATIONS FOR DESIGN OF LIGANDS BASED ON CHIRAL BIARYLDIAMINES," J. Am. Chem. Soc. 122:7132-7133; Liang, J.-L. et al. (2002) "METALLOPORPHYRIN-MEDIATED ASYMMETRIC NITROGEN-ATOM TRANSFER TO HYDROCARBONS: AZIRIDINATION OF ALKENES AND AMIDATION OF SATURATED C—H BONDS Catalyzed By Chiral Ruthenium And Manganese Porphyrins," Chem. Eur. J. 8:1563) for which catalysis via dirhodium(II,II) complexes ($Rh_2^{4+}$) holds a prominent position (Müller, P. et al. (1996) "A Method For Rhodium(II)-Catalyzed Aziridination Of Olefins," Tetrahedron 52:1543; Müller, P. et al. (1998) "The Rhodium(II)-Catalyzed Aziridination Of Olefins With\{[(4-Nitrophenyl)Sulfonyl]Imino\}Phenyl-Bold Lambda 3-Iodane," Can. J. Chem. 76:738-750; Guthikonda, K. et al. (2002) "A Unique and Highly Efficient Method for Catalytic Olefin Aziridination," J. Am. Chem. Soc. 124:13672; Liang, J.-L. et al. (2002) "Rhodium(II,II) Dimer as an Efficient Catalyst for Aziridination of Sulfonamides and Amidation of Steroids," Org. Lett. 4:4507; Liang, J. L. et al. (2003) "Chiral Rhodium(II,II) Dimers Catalyzed Enantioselective Intramolecular Aziridination Of Sulfonamides And Carbamates," Tetrahedron Lett. 44:5917; Fruit, C. et al. (2004) "Asymmetric Transfer Of Nitrenes Catalyzed By Chiral Dirhodium(II) Using Aromatic Sulfamate Esters," Tetrahedron-Asymmetry 15:1019). However, drawbacks in the uses of this methodology arise from high catalyst loadings, limited shelf life of TsN=IPh, competing C—H insertion, and/or poor selectivity.

Ruthenium, silver and copper catalysts have been studied in efforts to mediate more efficient direct aziridination (Man, W. L. et al. (2004) "Direct Aziridination Of Alkenes By A Cationic (Salen)Ruthenium(VI) Nitrido Complex," J. Am. Chem. Soc. 126(47):15336-15337; Omura, K. et al. (2004) "Design Of A Robust Ru(Salen) Complex: Aziridination With Improved Turnover Number Using N-Arylsulfonyl Azides As Precursors," Chem. Commun. (Camb) 21(18):2060-2061; Cui, Y. et al. (2003) "Efficient Aziridination Of Olefins Catalyzed By A Unique Disilver(I) Compound," J. Am. Chem. Soc. 125(52):16202-16203; Gullick, J. et al. (2003) "Observation Of The Enhancement In Enantioselectivity With Conversion For The Aziridination Of Styrene Using Copper Bis(Oxazoline) Complexes," Chem. Commun. (Camb.) (22):2808-2809. Rhodium (II,II) dimers have also been reported as aziridination catalysts (Liang, J. L. et al. (2002) "Rhodium(II,II) Dimer As An Efficient Catalyst For Aziridination Of Sulfonamides And Amidation Of Steroids," Org. Lett. 4(25):4507-4510).

Unfortunately, despite all such advances, methods for directly forming aziridines remain of limited utility, due to yield, cost, complexity or lack of stereospecificity. Thus, a need remains for a chemical synthetic approach capable of efficiently forming aziridines and possessing stereospecific control. The present invention is directed to this and other needs. The present invention is thus directed to a mild, selective, and efficient aziridination protocol that involves catalysis by a mixed-valent dirhodium(II,III) catalyst ($Rh_2^{5+}$).

SUMMARY OF THE INVENTION

This invention relates to compositions and methods for achieving the efficient aziridination of organic molecules, especially olefins. More specifically, the invention is directed to a mild, selective, and efficient aziridination protocol that involves catalysis by a mixed-valent dirhodium(II,III) catalyst ($Rh_2^{5+}$). Especially preferred are dirhodium (II,III) paddlewheel complexes, and especially dirhodium II,III paddlewheel complexes in which the arms of the paddlewheels are dirhodium carboxamidates. The invention particularly concerns dirhodium(II,III) carboxamidates catalyst that comprise seven-membered rings, such as dirhodium(II,III) caprolactamate, and their derivatives and analogues. More specifically, the invention provides a mild, efficient, and selective aziridination of olefins catalyzed by a mixed-valent dirhodium(II,III) catalyst ($Rh_2^{5+}$) that is a derivative or analogue of a dirhodium(II,II) compound. Especially preferred for this purpose are dirhodium (II,II) compounds that comprise paddlewheel complexes, and more especially dirhodium (II,II) compounds comprising paddlewheel complexes in which the arms of the paddlewheels are dirhodium carboxamidates. The invention particularly concerns the use of dirhodium(II,II) carboxamidates compounds that comprise seven-membered rings, such as dirhodium(II,III) caprolactamate, and their derivatives and analogues to form the mixed-valent dirhodium(II,III) catalyst ($Rh_2^{5+}$) of the present invention. More specifically, the invention provides a mild, efficient, and selective aziridination of olefins catalyzed by a derivative or analogue of a dirhodium(II,II) caprolactamate [$Rh_2(cap)_4$]. Using p-toluenesulfonamide ($TsNH_2$), N bromosuccinimide (NBS), and potassium carbonate, aziridines are readily obtained with isolated yields up to 95% under extremely mild conditions with as little as 0.01 mol % $Rh_2(cap)_4$. Aziridine formation occurs through $Rh_2^{5+}$ catalyzed aminobromination and subsequent base-induced ring closure. An X-ray crystal structure of an $Rh_2^{5+}$ halide complex, formed from the reaction between $Rh_2(cap)_4$ and N chlorosuccinimide confirms these conclusions. The aziridination reaction may be illustrated as follows:

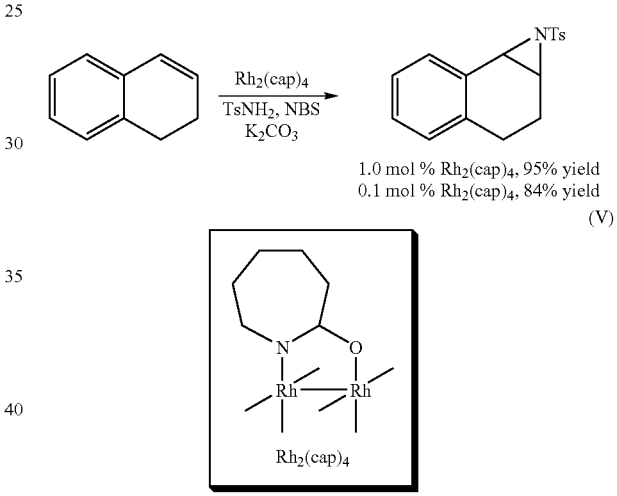

1.0 mol % $Rh_2(cap)_4$, 95% yield
0.1 mol % $Rh_2(cap)_4$, 84% yield (V)

In detail, the invention concerns a method for producing an aziridine compound, which comprises reacting an olefin with a mixed-valent dirhodium(II,III) catalyst ($Rh_2^{5+}$) under conditions sufficient to convert the olefin into the aziridine compound.

The invention particularly concerns the embodiment of such method wherein the a mixed-valent dirhodium(II,III) catalyst ($Rh_2^{5+}$) is an analogue or derivative of a member of the carboxamidate class of dirhodium(II,II) paddlewheel complexes, and especially wherein the arms of the carboxamidate class of dirhodium(II,II) paddlewheel complexes comprises seven membered rings, and even more particularly wherein the mixed-valent dirhodium(II,III) catalyst ($Rh_2^{5+}$) is dirhodium(II,II) caprolactamate [$Rh_2(cap)_4$], or a derivative or analogue thereof.

The invention further concerns the embodiments of such methods wherein the mixed-valent dirhodium(II,III) catalyst ($Rh_2^{5+}$) catalyzes the conversion of the olefin to the aziridine compound via an aminobromination reaction.

The invention further concerns the embodiments of such methods wherein the olefin is reacted with the mixed-valent dirhodium(II,III) catalyst (Rh$_2^{5+}$) in the presence of p-toluenesulfonamide (TsNH2), N bromosuccinimide (NBS), and potassium carbonate.

The invention further concerns the embodiments of such methods wherein the aziridine compound comprises a structure selected from the group consisting of the structures:

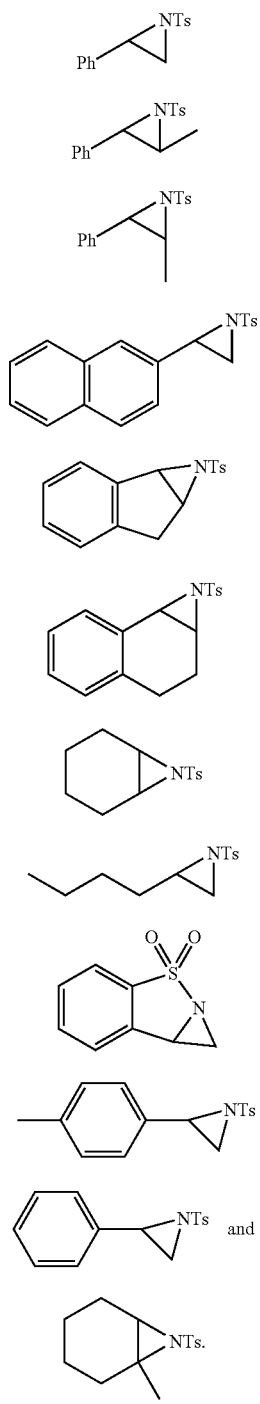

The invention further concerns a catalyst that mediates an olefin aziridination reaction through the formation of an intermediate having the structures (VI) or (VII):

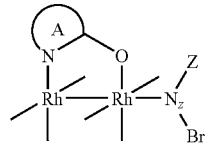

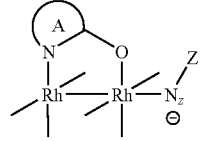

wherein A is a ring structure that may be substituted or unsubstituted, N$_z$ is nitrogen and Z is an optionally substituted aryl moiety that increases the electophilicity of Nz. A preferred group Z is p-tolunesulfonamide.

The invention further concerns the embodiments of such catalysts wherein A is a seven-membered ring or a derivative or analogue thereof, and more particularly wherein A is a caprolactamate ring, or a derivative or analogue thereof. The invention additionally concerns the embodiments of such catalyst wherein Z is a toluenesulfonimidyl moiety.

The invention further concerns the embodiments of such catalysts wherein the intermediate (VI) or (VII) is formed by reacting a dirhodium(II,II) compound having the structure:

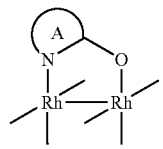

in the presence of an olefin, p-toluenesulfonamide (TsNH2), N bromo-succinimide (NBS), and potassium carbonate.

BRIEF DESCRIPTION OF THE FIGURES

FIG. 1A shows a graphical representation, FIG. 1B shows a "ball and stick" representation. FIG. 1C shows a stereoimage of the structure.

DESCRIPTION OF THE PREFERRED EMBODIMENTS

Figure 1A:
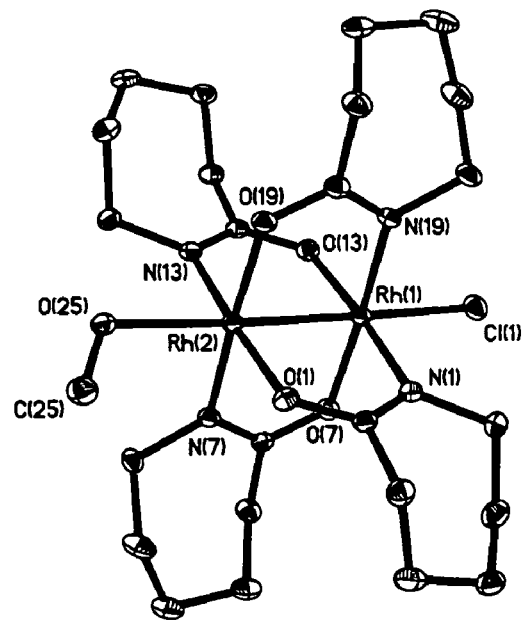
FIG. 1A, FIG. 1B and FIG. 1C show the deduced crystallographic structure of compound 2 of Scheme 2.

Compounds comprising the transition metals: cobalt, copper, manganese, rhodium, rhuthenium and silver, have been found to have potential as aziridination catalysts (see, for example, Gao, G. Y. et al. (2005) "COBALT-CATALYZED EFFICIENT AZIRIDINATION OF ALKENES," Org Lett. 7(15):3191-3193; Mohr, F. et al. (2005) "A practical, fast, and high-yielding aziridination procedure using simple Cu(II) complexes containing N-donor pyridine-based ligands," J. Org. Chem. 70(12): 4833-4839; Liang, J.-L. et al. (2002) "METALLOPORPHYRIN-MEDIATED ASYMMETRIC NITROGEN-ATOM TRANSFER TO HYDROCARBONS: AZIRIDINATION OF ALKENES AND AMIDATION OF SATURATED C—H Bonds Catalyzed By Chiral Ruthenium And Manganese Porphyrins," Chem. Eur. J. 8:1563; Padwa, A. et al. (2004) "Riodium(II)-Catalyzed Aziridination Of Allyl-Substituted Sulfonamides And Carbamates," J. Org. Chem. 69(19):6377-6386; Catino, A. J. et al. (2005) "Efficient Aziridination Of Olefins Catalyzed By Mixed-Valent Dirhodium(II,III) Caprolactamate," Org. Lett. 7(13):2787-2790; Cui, Y. et al. (2003) "Efficient Aziridination Of Olefins Catalyzed By A Unique Disilver(I) Compound," J. Am. Chem. Soc. 125(52):16202-16203).

This invention relates to compositions and methods for achieving the efficient aziridination of organic molecules, especially olefins. More specifically, the invention is directed to a mild, selective, and efficient aziridination protocol that involves catalysis by a mixed-valent dirhodium(II,III) catalyst ($Rh_2^{5+}$). The present invention derives in part from the recognition that rhodium compounds, and in particular, dirhodium (II,II) "paddlewheel" complexes can be made to undergo a transformation to form mixed-valent dirhodium (II,III) "paddlewheel" complexes that exhibit desirable aziridination catalytic ability. As used herein, a dirhodium (II,II) "paddlewheel" complex is a molecule having the general schematic structure (I), in which two rhodium ions are bonded together and their coordinate x,y,z axes are components of ring structures, so as to form a "paddlewheel-like" shape.

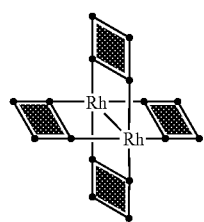

(I)

Exemplary dirhodium (II,II) "paddlewheel" complexes are disclosed by: Doyle, M. P. et al. (2001) "The Influence of Ligands on Dirhodium(II) ON Reactivity and Selectivity in Metal Carbene Reactions," Prog. Inorg. Chem. 49:113-168, Ren, T. (1998) "Substituent Effects in Dinuclear Paddlewheel Compounds: Electrochemical and Spectroscopic Investigations," Coord. Chem. Rev. 175:43-58; Lutterman, D. A. (2005) "Photoinduced One-Electron Reduction of Alkyl Halides by Dirhodium(II,II) Tetraformamidinates and a Related Complex with Visible Light," Inorg. Chem. 44:5388-5396; Angeles-Boza, A. M. et al. (2004) "DNA Binding and Photocleavage in Vitro by New Dirhodium(II) dppz Complexes: Correlation to Cytotoxicity and Photocytotoxicity," Inorg. Chem. 43:8510-8519; Dequeant, M. Q. et al. (2004) "Dirhenium Paddlewheel Compounds Supported by N,N'-Dialkylbenzamidinates: Synthesis, Structures, and Photophysical Properties," Inorg. Chem. 43:7887-7892; Berry, J. F. et al. (2005) "A Hardwon Dirhodium Paddlewheel With Guanidinate Type (Hpp) Bridging Ligands," Dalton Trans. 7;(23):3713-3715; Cotton, F. A. et al. (2002) "The First Dirhodium Tetracarboxylate Molecule Without Axial Ligation: New Insight Into The Electronic Structures Of Molecules With Importance In Catalysis And Other Reactions," J. Am. Chem. Soc. 2002 124(20):5658-5660; Sorasaenee, K. et al. (2003) "Isolation of the Novel Dirhodium(II/II) Thiolate Compound $Rh2(\eta^1-C_6H_5S)_2(\mu-C_6H_5S)_2(bpy)_2$," 42(3):661-663; Takazaki, Y. et al. (2003) "A Honeycomb Network Of A Paddlewheel-Type Dirhodium Complex In Two Oxidation States And Pinning Of The Oxidation States," Chem. Lett. 32(2):120; and Chifotides, H. T. et al. (2005) "Interactions of Metal-Metal-Bonded Antitumor Active Complexes with DNA Fragments and DNA," Acc. Chem. Res. 38:146-156.

Of particular relevance to the present invention is the dirhodium carboximate class of dirhodium (II,III) "paddlewheel" complexes. Especially preferred are dirhodium(II,II) complexes in which the arms of the paddlewheels are dirhodium(II,II) carboxamidates. Even more preferred are dirhodium(II,II) carboxamidates paddlewheel complexes that comprise seven-membered rings, such as dirhodium(II,II) caprolactamate, and their derivatives and analogues. Dirhodium(II,II) caprolactamate, and their derivatives and analogues are the particularly preferred sources for forming the mixed-valent dirhodium (II,III) catalysts of the present invention. The dirhodium carboximate class of dirhodium (II,II) "paddlewheel" complexes has the general structure (II):

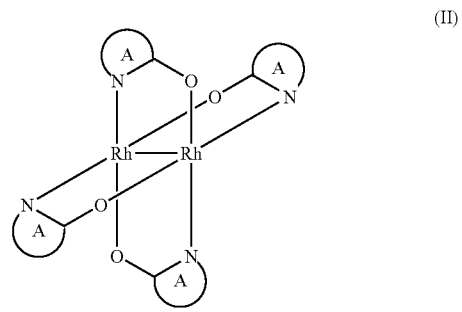

(II)

wherein A is a ring structure that may be substituted or unsubstituted.

The dirhodium carboximate class of dirhodium (II,II) "paddlewheel" complexes are used for enatioselective carbene transformations (e.g., cyclopropanation, cyclopropenation, and insertion into activated carbon-hydrogen bonds), and are discussed by Doyle, M. P. et al. (1993) "Dirhodium(II) Tetrakis(Carboxamidates) with Chiral Ligands. Structure and Selectivity in Catalytic Metal Carbene Transformations," J. Am. Chem. Soc. 115:9968-9978; Doyle, M. P. et al. (1995) "Highly Enantioselective Route to β-Lactams via Intramolecular C—H Insertion Reactions of Diazoacetylazacycloalkanes Catalyzed by Chiral Dirhodium(II) Carboxamidates," Synlett 1075-1076; Doyle, M. P. (1995) "Enantiomer Differentiation in Intramolecular Carbon-Hydrogen Insertion Reactions of Racemic Secondary Alkyl Diazoacetates Catalyzed by Chiral Dirhodium(II) Carboxamidates," Russ. Chem. Bull. 44:1729-1734; Doyle, M. P. et al. (1995) "Enhancement of Enantiocontrol/Diasthreocontrol in Catalytic Intramolecular Cyclopropanation and Carbon-Hydrogen Insertion Reactions of Diazoacetates with Rh2(4S-MP-PIM)4" Tetrahedron Lett. 36:7579-7582; Doyle, M. P. et al. (1995) "Optimization of Enantiocontrol for Carbon-Hydrogen Insertion with Chiral Dirhodium(II) Carboxamidates. Synthesis of Natural Dibenzylbutyrolactone Lignans from 3-Aryl-1-propyl Diazoacetates in High Optical Purity," J. Org. Chem. 60:6654-6655; Doyle, M. P. et al. (1996) "Highly Enantioselective Intramolecular Cyclopropanation Reactions of N-Allylic-N-Methyldiazoacetamides Catalyzed by Chiral Dirhodium(II) Carboxamidates," J. Org. Chem. 61:2179-2184 (1996); Doyle, M. P. et al. (1996) "Chiral Dirhodium Carboxamidates. Catalysts for Highly Enantioselective Syntheses of Lactones and Lactams," Aldrichimica Acta 29(1):3-11; Bode, J. W. et al. (1996) "Intramolecular Regioselective Insertion into Unactivated Prochiral Carbon-Hydrogen Bonds with Diazoacetates Catalyzed by Chiral Dirhodium(II) Carboxamidates. Highly Enantioselective Total Synthesis of Natural Lignan Lactones," J. Org. Chem. 61:9146-9155; Doyle, M. P. etal. (1997) "Highly Enantioselective Oxonium Ylide Formation and Stevens Rearrangement Catalyzed by Chiral Dirhodium(II) Carboxamidates," Tetrahedron Lett. 38:4367-4370; Roos, G. H. P. et al. (1998) "Synthesis, Structure, and Reactivity of a Novel Series of Diastereomeric Dirhodium(II) TetraCarboxamidates. Catalysts for Asymmetric Diazoacetate Transformations," Aust. J. Chem. 51:1-8; Doyle, M. P. et al. (1998) "Recent Advances in Asymmetric Catalytic Metal Carbene Transformations," Chem. Rev. 98:911-935; Doyle, M. P. et al. (1998) "Enantiocontrol in the Generation and Diastereoselective Reactions of Oxonium Ylides Catalyzed by Chiral Dirhodi(II) Carboxamidates. Metal-Stabilized Ylides as Reaction Intermediates," J. Am. Chem. Soc. 120:7653-7654; Doyle, M. P. et al. (2000) "Dirhodium(II) Tetrakis[methyl 2-oxaazetidine-4-carboxylate]: A Chiral Dirhodium(II) Carboxamidate of Exceptional Reactivity and Selectivity," Organic Lett. 2:1145-1147; Doyle, M. P. et al. (2000) "Optimization of Enantiocontrol in cis-Selective Cyclopropanation Reactions Catalyzed by Dirhodium(II) Tetrakis-[alkyl 2-oxaazetidine-4(S)-carboxylates]," J. Chem. Soc. Chem. Commun. 867-868; Doyle, M. P. et al. (2001) "Reactivity Enhancement for Chiral Dirhodium(II) Tetrakis (Carboxamidates)," Adv. Synth. Cat. 343(1): 112-117; Doyle, M. P. et al. (2001) "A New Class of Chiral Lewis Acid Catalysts for Highly Enantioselective Hetero-Diels-Alder Reactions: Exceptionally High Turnover Numbers from Dirhodium(II) Carboxamidates," J. Am. Chem. Soc. 123: 5366-5367; Doyle, M. P. et al. (2001) "High Selectivity from Configurational Match/Mismatch in Carbon-Hydrogen Insertion Reactions of Steroidal Diazoacetates Catalyzed by Chiral Dirhodium(II) Carboxamidates," J. Org. Chem. 66:8112-8119; Doyle, M. P. et al. (2002) "Highly Selective Synthesis of a 2-Deoxyxylolcatam via Enantioselective Carbon-Hydrogen Insertion Reactions Using Chiral Dirhodium (II) Carboxamidates," Adv. Synth. Cat. 344:91-95; Doyle, M. P. et al. (2002) "Enantioselective Carbon-Hydrogen Insertion is an Effective and Efficient Methodology for the Synthesis of (R)-(−)-Baclofen," Chirality 14:169-172; Doyle, M. P. et al. (2002) "Total Synthesis of (S)-(+)-Imperanene. Effective use of Regio- and Enantioselective Intramolecular Carbon-Hydrogen Insertion Reactions Catalyzed by Chiral Dirhodium(II) Carboxamidates," J. Org. Chem. 67:2954-2959; and by Doyle, M. P. et al. (2002) "Preparation and Catalytic Properties of Immobilized Chiral Dirhodium(II) Carboxamidates," Organometallics 21:1747-1749).

Examples of members of the dirhodium carboximate class of dirhodium (II,II) "paddlewheel" complexes are ring structures, such as (III):

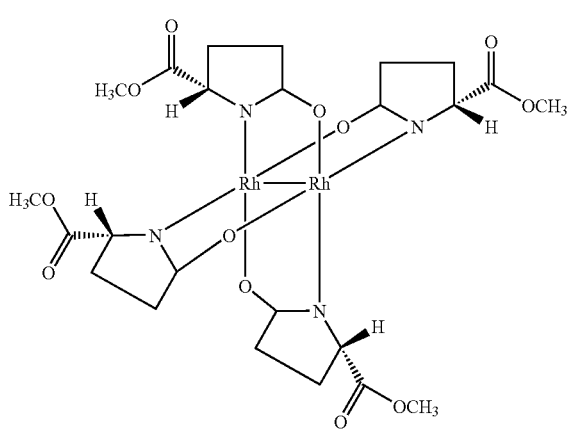

(III)

(wherein A of the general structure shown in (II) is methanesulfonyl azide (mesyl azide) ("MEPY")) and (IV):

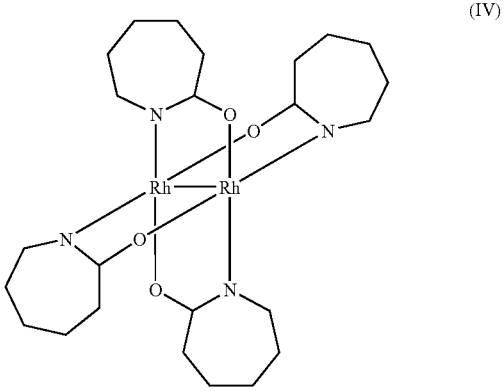

(IV)

(wherein A of the general structure (II) is a lactamate ring (especially a caprolactamate ring as shown in (IV)), as well as derivatives or analogues of such compounds.

To facilitate the illustration of the dirhodium(II,II) "paddlewheel" compounds of the present invention, such molecules are typically represented herein by showing only one of their four "paddlewheel" A arms and omitting the structures of their remaining three "paddlewheel" A arms. Thus, for example, structures (V) and (IV) illustrate the same compound. It is, however, to be understood that the unbonded bonds of the rhodium atoms in such depictions (see, e.g., structures 1, 2, 13, V, VI, VII, VIII, etc.) are bonded to unshown A moieties. As will be appreciated, the bond lengths and angles in all of the depicted structures herein are not shown to scale.

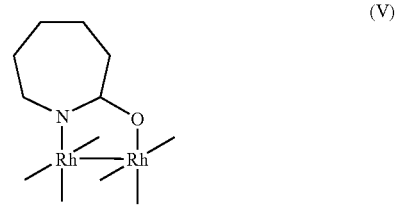

(V)

Dirhodium(II,II) caprolactamate (referred to herein as "$Rh_2(cap)_4$") is the preferred aziridination catalyst of the present invention. $Rh_2(cap)_4$ exhibits a shallow redox potential ($E_{1/2}$=11 mV); $Rh_2(cap)_4 \rightarrow Rh_2(cap)_4^+$<1 kcal/mol (Doyle, M. P. et al. (2001) In: *Progress in Inorganic Chemistry*; volume 49:113, Karlin, K., Ed; Wiley: New York. Dirhodium(II,II) caprolactamate (IV/V) has been found to perform admirably as a catalyst for allylic oxidation (Catino, A. J. et al. (2004) "Dirhodium(II) Caprolactamate: An Exceptional Catalyst for Allylic Oxidation," J. Am. Chem. Soc. 126(42):13622-13623). Its effectiveness is derived in part from its ability to undergo facile atom-transfer redox chemistry ($Rh_2^{4+} \leftrightarrows Rh_2^{5+}$) because of its low one-electron oxidation potential.

The present invention is directed to such catalysts as well as to their derivatives and analogues and the use of such derivatives and analogues. As used herein, an "analogue" of a recited dirhodium(II,II) "paddlewheel" compound is a compound that possesses the dirhodium(II,II) "paddlewheel" structure of the recited compound, but contains or lacks one or more functional groups or atoms relative to the recited compound. Thus, for example, compound 2 is an analogue of compound (V). As used herein, a "derivative" of a recited dirhodium(II,II) "paddlewheel" compound is a compound that possesses the dirhodium(II,II) "paddlewheel" structure of the recited compound, but contains or lacks one or more functional groups or atoms relative to the recited compound, and was derived from the recited compound. Mixed-valent dirhodium (II,III) compounds are thus an example of a derivative of a dirhodium(II,II) compound. Thus, for example, compound 1 is a derivative of compound (V).

The present invention derives in part from the recognition that $Rh_2(cap)_4$ exhibits potential of as a bromine atom-transfer redox catalyst. In this regard, $Rh_2(cap)_4$ is found to undergo a one-electron oxidation in the presence of N-bromosuccinimide (NBS) to yield the paramagnetic complex 1 of Scheme 1).

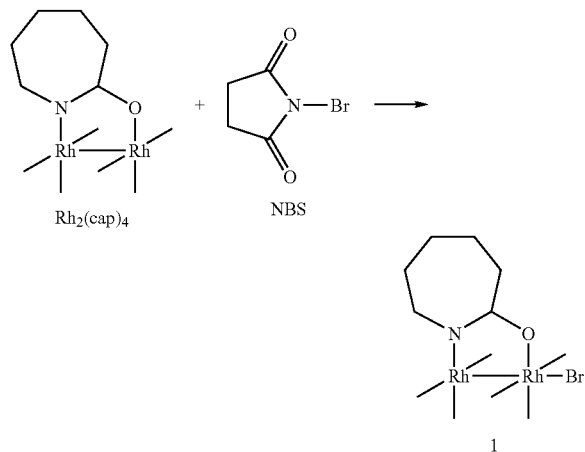

Evidence of the reaction includes an oxidative color change (light blue→deep red) in $CH_2Cl_2$ (the UV/visible spectrum of the rhodium complex upon addition of NBS contains a low energy absorption (δ-δ* transition) at 971 nm ($\epsilon$=930 M$^{-1}$ cm$^{-1}$) indicating a $Rh_2^{5+}$ species (Cotton, F. A. et al. (1982) In: *Multiple Bonds Between Metal Atoms*, page 390, Wiley, New York; Cotton, F. A. et al. (1993)In: *Multiple Bonds Between Metal Atoms*, 2nd ed., page 475; Oxford: New York.

Figure 1B:
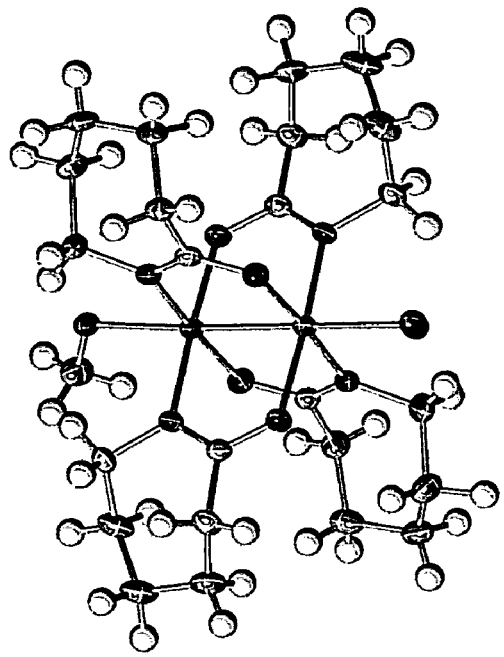
Figure 1C:
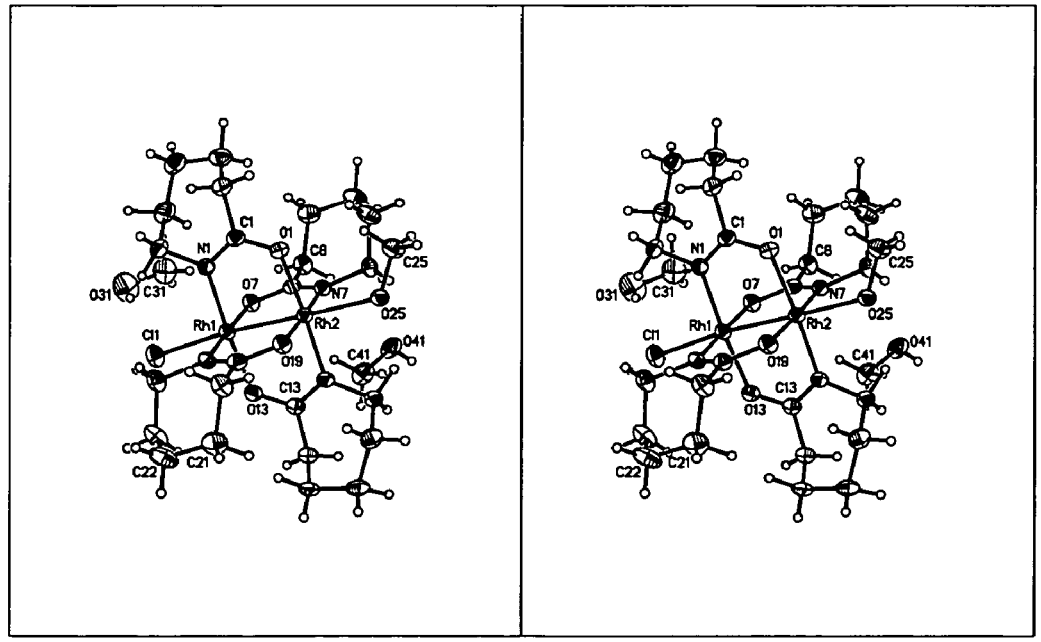
Figure 2:
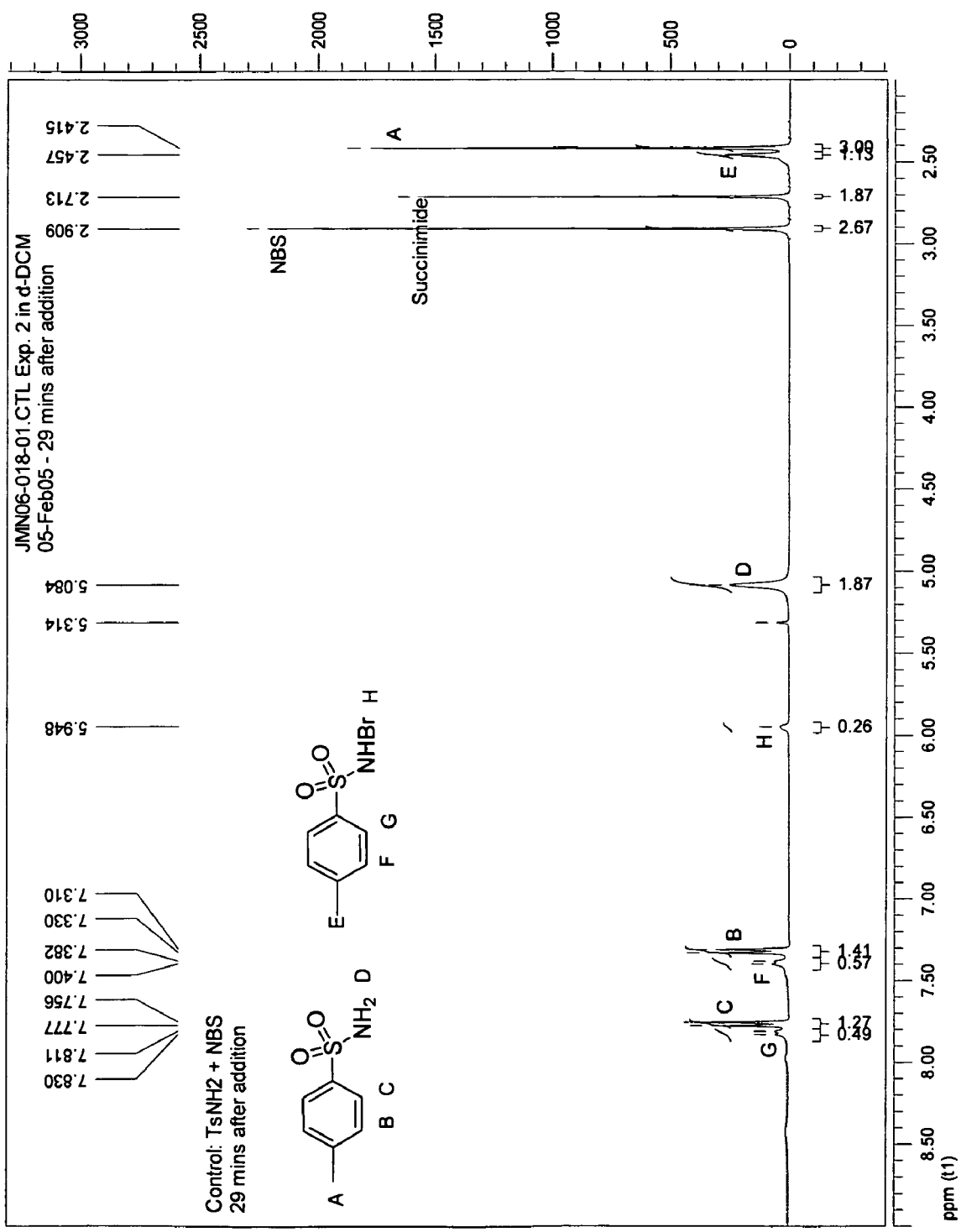
FIG. 2 shows the results of NMR studies on the Rh$_2$(cap)$_4$ catalysts of the present invention.

By replacing NBS with N chlorosuccinimide (NCS), suitable crystals were obtained for X-ray analysis. The crystallographic data revealed that the dirhodium complex contained an axially bound chlorine (compound 2 of Scheme 2; FIG. 1A, FIG. 1B, FIG. 1C). The spectral properties of the product are consistent with a dirhodium(II,III) complex, and thus provide indirect support for the conclusion that the described reaction products were in fact obtained.

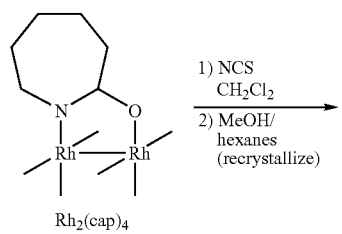

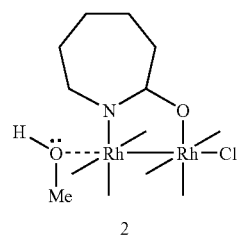

In order to determine if $Rh_2(cap)_4$ and NBS could be synthetically useful, a bromine-catalyzed aziridination was considered (Jeong, J. U. et al. (1998) "BROMINE-CATALYZED AZIRIDINATION OF OLEFINS. A RARE EXAMPLE OF ATOM-TRANSFER REDOX CATALYSIS BY A MAIN GROUP ELEMENT," J. Am. Chem. Soc. 1998, 120(27): 6844-6845; Ali, S. I. et al. (1999) "PYRIDINIUM HYDROBROMIDE PERBROMIDE: A VERSATILE CATALYST FOR AZIRIDINATION OF OLEFINS USING CHLORAMINE-T," Org. Lett. 1(5); 705-707; Dauban, P. et al. (2001) "INTRAMOLECULAR BROMINE-CCATALYZED AZIRIDINATION: A NEW DIRECT ACCESS TO CYCLIC SULFONAMIDES," Tetrahedron Lett. 42:1037-1040; Thakur, V. V. et al. (2003) "N-BROMOAMIDES AS VERSATILE CATALYSTS FOR AZIRIDINATION OF OLEFINS USING CHLORAMINE-T," Tetrahedron Lett. 44:989-992; Jain, S. L. et al. (2004) "AN EFFICIENT TRANSITION METAL-FREE AZIRIDINATION OF ALKENES WITH CHLORAMINE-T USING AQUEOUS $H_2O_2$/HBR," Tetrahedron Lett. 45:8731-8732).

The protocol of Jeong, J. U. et al. (1998) ("BROMINE-CATALYZED AZIRIDINATION OF OLEFINS. A RARE EXAMPLE OF ATOM-TRANSFER REDOX CATALYSIS BY A MAIN GROUP ELEMENT," J. Am. Chem. Soc. 1998, 120(27): 6844-6845) offers unique advantages over nitrene delivery; however, the catalytic efficiency of phenyltrimethyl-ammonium tribromide and the formation of 1,2-dibromide by-products were noted limitations.

Efforts using Chloramine-T as a nitrogen source with product 1 of Scheme 1 as a catalyst yielded only trace amounts of aziridine due to catalyst decomposition under the reaction conditions. For this reason, the feasibility of a less basic amine derivative to mitigate catalyst destruction was investigated. Toward this end, treating 4-methylstyrene (1.0 equiv) in $CH_2Cl_2$ (0.27 M/olefin) with p-toluenesulfonamide ("$TsNH_2$") (1.1 equiv), and 0.1 mol % $Rh_2(cap)_4$ followed by NBS (1.1 equiv) rapidly gave β-bromosulfonamide 3 in 95% isolated yield (Scheme 3). By $^1$H NMR, 70% conversion (from 4-methylstyrene into 3) was observed in only 3 mins at 1 mol % $Rh_2(cap)_4$. This result was complimentary to the observation of bromoamidation of olefms with $TsNH_2$ and NBS using 5 mol % of various Lewis-acids (Thakur, V. V. et al. (2003) "TRANSITION METAL-CATALYZED REGIO- AND STEREOSELECTIVE AMINOBROMINATION OF OLEFINS WITH TsNH2 AND NBS AS NITROGEN AND BROMINE SOURCES," Org. Lett. 5(6):861-864).

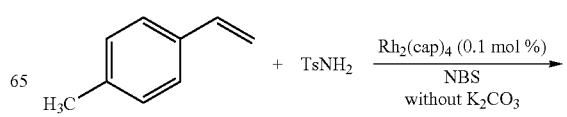

-continued

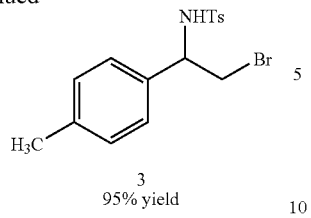

3
95% yield

-continued

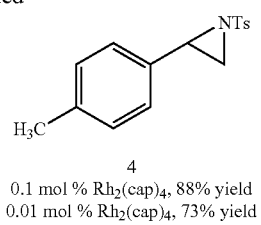

4
0.1 mol % Rh$_2$(cap)$_4$, 88% yield
0.01 mol % Rh$_2$(cap)$_4$, 73% yield

The reactions demonstrated the comparative efficiency of Rh$_2$(cap)$_4$ for bromoamidation. In order to convert the product directly to aziridines, the same reaction was conducted in the presence of K$_2$CO$_3$ (2.1 equiv). Aziridine 4 was produced in 88% isolated yield after 12 hours (Scheme 4). Further, reducing the amount of catalyst to only 0.01 mol % Rh$_2$(cap)$_4$ (substrate:catalyst=1:10,000) gave 4 in 73% yield in 12 hours.

This operationally straightforward reaction was readily extended to a variety of olefins (Table 1), however, electron-deficient (methyl-trans-cinnamate), tri-substituted (1-methylcyclohexene), and α,α-disubstituted (α-methylstyrene) olefins were not reactive substrates for this protocol. Example 1 provides a representative synthetic procedure for forming aziridines. Aryl- and alkyl-substituted alkenes underwent inter- and intramolecular aziridination in high yield under these mild conditions. Trans-aminobromination occurred exclusively for cycloalkenes prior to aziridine formation, and C—H insertion products were not observed for aliphatic olefins (e.g., entry 9 of Table 1).

Scheme 4

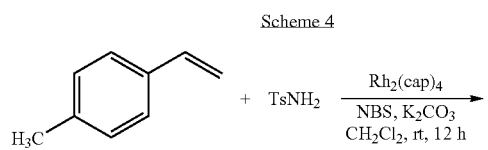

TABLE 1

Rh$_2$(cap)$_4$ Catalyzed Aziridination of Olefins

| Entry | Olefin | Aziridine | Rh$_2$(cap)$_4$ (mol %) | Yield$^a$ (%) |
|---|---|---|---|---|
| 1 | Ph⌢⌢ | Ph-aziridine-NTs | 1.0 / 0.1 | 77 / 62 |
| 2 | Ph-CH=CH-CH$_3$ | Ph-aziridine(Me)-NTs | 1.0 | 69$^b$ |
| 3 | Ph-CH$_2$-CH=CH$_2$ | Ph-CH$_2$-aziridine-NTs | 1.0 | 77$^b$ |
| 4 | naphthyl-vinyl | naphthyl-aziridine-NTs | 0.1 | 65 |
| 5 | indene | indene-NTs-aziridine | 0.1 | 88 |
| 6 | dihydronaphthalene | dihydronaphthalene-NTs-aziridine | 1.0 / 0.1 | 95 / 84 |
| 7 | cyclooctene | cyclooctene-NTs-aziridine | 1.0 | 74$^c$ |

TABLE 1-continued

Rh$_2$(cap)$_4$ Catalyzed Aziridination of Olefins

| Entry | Olefin | Aziridine | Rh$_2$(cap)$_4$ (mol %) | Yield$^a$ (%) |
|---|---|---|---|---|
| 8 | cyclohexene | N-Ts norcarane-type aziridine | 1.0 | 60$^c$ |
| 9 | 1-pentene | 2-propyl-N-Ts aziridine | 1.0 | 77 |
| 10 | 2-vinylbenzenesulfonamide | fused benzosultam aziridine | 0.1 | 86 |
| 11 | 2-allylbenzenesulfonamide | fused benzosultam aziridine | 1.0 | 87 |
| 12 | 4-methylstyrene | 4-methylstyrene N-Ts aziridine | 1.0 | 99 |
| 13 | 4-methylstyrene | 4-methylstyrene N-Ts aziridine | 0.1 | 88 |
| 14 | 4-methylstyrene | 4-methylstyrene N-Ts aziridine | 0.01 | 73 |
| 15 | styrene | styrene N-Ts aziridine | 0.1 | 62 |
| 16 | 1-methylcyclohexene | 1-methyl N-Ts norcarane-type aziridine | 0.1 | 11 |

$^a$Isolated yield after purification;
$^b$Under these reaction conditions, aziridine diasterioselectivity was determined by $^1$H NMR prior to silica purification, entry 2 (trans/cis = 4:1), entry 3 (cis/trans = 7:1);
$^c$Using 5 equiv. of olefin, yield based on p-TsNH$_2$ Without in any manner intending to be limited thereby, a mechanistic proposal for the observed aziridination reaction is presented in Scheme 5. From analysis of a stoichiometric mixture of NBS and TsNH$_2$ in solution, it was concluded that an equilibrium mixture of N-bromo-p-toluensulfonamide (TsNHBr, 5) and succinimide (Equation 1) existed. Complete conversion of 5 to NBS was observed by addition of excess succinimide, thereby confirming an equilibrium process. Moreover, addition of Rh$_2$(cap)$_4$ did not change the equilibrium position, although a small amount of N,N-dibromo-p-toluenesulfonamide (TsNBr$_2$) was observed after 24 hours.

When excess K$_2$CO$_3$ was added to the equilibrium mixture (NBS, TsNHBr/TsNH$_2$, and succinimide), a precipitate was formed concomitant with the disappearance of both NBS and 5 by $^1$H-NMR analysis (Equation 2). Because of the low pKa of 5 (TsNHCl pKa=4.55; Morris, J. C. et al. (1948) "EQUILIBRIUM STUDIES ON N-CHLORO COMPOUNDS. I. THE IONIZATION CONSTANT OF N-CHLORO-P-TOLUENESULFONAMIDE," J. Am. Chem. Soc. 70(6):2036-2041; Rangappa, K. S. "MECHANISTIC STUDIES OF THE OXIDATION OF SUBSTITUTED PHENETHYL ALCOHOLS BY N-METALLO-N-HALOARYLSULPHONAMIDES: KINETIC ISOTOPE STUDIES," J. Phys. Org. Chem. 14(10):684-690) deprotonation shifts the equilibrium towards 6. Isolation of the precipitate and subsequent $^1$H-NMR analysis in d-DMSO indicated that the precipitate was indeed 6.

Scheme 5

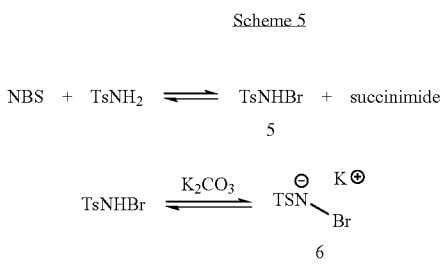

(Equation 1)

NBS + TsNH₂ ⇌ TsNHBr + succinimide
                      5

(Equation 2)

TsNHBr $\xrightleftharpoons{K_2CO_3}$ TsN$^\ominus$ K$^\oplus$
                                          \Br
                                    6

The role of the dirhodium catalyst in the reaction was investigated. The observed regioselectivity of 3.is consistent with an ionic addition mechanism (i.e., a bromonium-ion intermediate) (Hassner, A. et al. (1968) "STEREOCHEMISTRY. XXXIX. IONIC AND FREE-RADICAL ADDITION OF BROMINE AZIDE TO OLEFINS," Am. Chem. Soc. 90(1):216-218). Evidence against the intermediacy of a nitrene under the conditions described in Scheme 4 and Table 1 was provided by the failure of 7 to undergo C—H insertion under the reaction conditions (Equation 3).

(Equation 3)

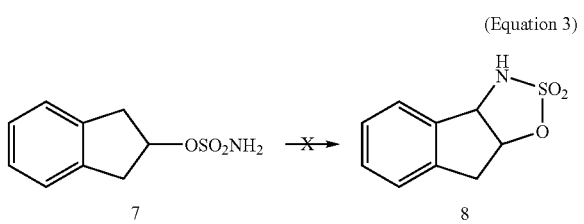

A bromonium-ion intermediate was further implicated by the use of a radical (and cation) probe 9 (Newcomb, M. et al. (1992) "PICOSECOND RADICAL KINETICS. RING OPENINGS OF PHENYL-SUBSTITUTED CYCLOPROPYLCARBINYL RADICALS," J. Am. Chem. Soc. 114(27):10915-10921) that gave only ring-opened product 10 under the reaction conditions with and without K₂CO₃ (Equation 4).

(Equation 4)

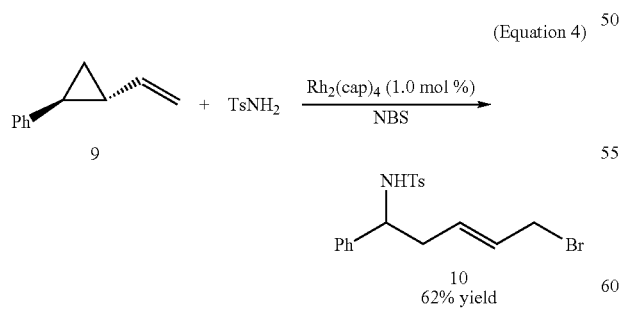

The above-reported investigations indicate that an ionic mechanism, as opposed to a nitrene process, is operative (bromine atom-transfer via a radical process is not operative as no bromine-addition products were observed when cyclohexene or p-methylstyrene were treated with NBS and Rh₂ (cap)₄ in CH₂Cl₂. Further, that a mixed-valent dirhodium(II,II) complex, such as 1, is a Lewis acid akin to dirhodium(II,II) carboxamidates (for dirhodium carboxamidates as Lewis acids see: Doyle, M. P. et al. (2001) "A NEW CLASS OF CHIRAL LEWIS ACID CATALYSTS FOR HIGHLY ENANTIOSELECTIVE HETERO-DIELS-ALDER REACTIONS: EXCEPTIONALLY HIGH TURNOVER NUMBERS FROM DIRHODIUM(II) CARBOXAMIDATES," J. Am. Chem. Soc. 123: 5366-5367; Anada, M. et al. (2004) "A NEW DIRHODIUM(II) CARBOXAMIDATE COMPLEX AS A CHIRAL LEWIS ACID CATALYST FOR ENANTIOSELECTIVE HETERO-DIELS-ALDER REACTIONS," Angew. Chem., Int. Ed., 43:2665; Doyle, M. P. et al. (2004) "ASYMMETRIC CATALYSIS SPECIAL FEATURE PART I: ASYMMETRIC HETERO-DIELS-ALDER REACTION CATALYZED BY DIRHODIUM(II) CARBOXAMIDATES," Proc. Natl. Acad. Sci. (U.S.A.) 101:5391-5395; Valenzuela, M. et al. (2004) "INFLUENCE OF THE DIENE IN THE HETERO-DIELS-ALDER REACTION CATALYZED BY DIRHODIUM(II) CARBOXAMIDATES," Synlett 13:2422; Forslund, R. E. et al. (2005) "CHIRAL DIRHODIUM(II) CARBOXAMIDATE-CATALYZED [2+2]-CYCLOADDITION OF TMS-KETENE AND ETHYL GLYOXYLATE," Adv. Synth. Catal. 347:87-92) is suggested by reaction inhibition in Lewis base solvents such as acetonitrile and THF. Moreover, dirhodium(II,III) methanol-complex 2 is capable of catalyzing the hetero-Diels-Alder (HDA) reaction of p-nitrobenzaldehyde and 1-methoxy-3-[(trimethylsilyl)oxy]-butadiene (Danishefsky diene). Therefore, again without limitation to the present invention, it is proposed that 1 activates residual amounts of 5 and/or NBS catalyzing electrophilic bromonium ion-transfer to an olefin to yield 11 (Scheme 6). Capture with TsNH₂ or 6, gives bromoamide 12 (Compound 12 (R=4-methylphenyl, X=Br) was independently synthesized by treatment of 4-methylstyrene with N,N-dibromo-p-toluenesulfonamide in CH₂Cl₂. It was found that 12 acts as an electrophilic source of bromine, as treatment with succinimide yields NBS and aminobromide 3 in an equilibrium mixture (see Examples)), which can undergo ring closure to give the aziridine.

Scheme 6

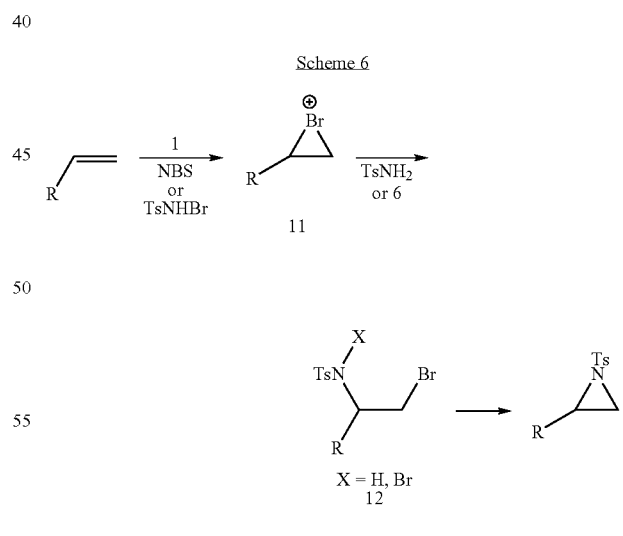

Dirhodium (II, III)
Lewis-acid activation of
NBS or TsNHBr

The reaction mechanism can be further elaborated as shown in Scheme 7.

Scheme 7

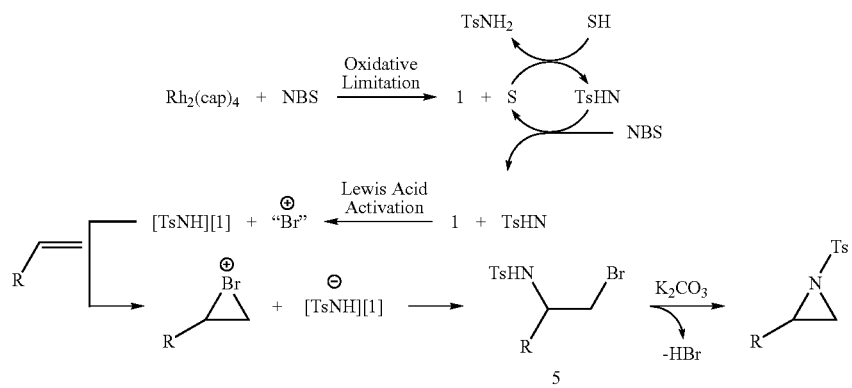

The metal-based Lewis-acid catalysts for aminobromination reported by Sudalai gave a moderate enhancement in yield for aziridination over a measurable background reaction. Without catalyst, aziridine 3 was obtained in 19% yield. Under the same conditions, other transition metals were examined giving 3 in moderate yield: CuI (5 mol %, 55%), CuI (1 mol %, 28%), Mn(II)-salen (5 mol %, 41%), $Rh_2(OAc)_4$ (1 mol %, 42%), $Rh_2(pfb)_4$ (1 mol %, 49%), $Rh_2(cap)_4$Cl (0.1 mol %, 52%), and $Rh_2(cap)_4$ (0.1 mol %, 88%). This enhancement may be due to the incompatibility of these Lewis acid catalysts and potassium carbonate under the reaction conditions. With the dirhodium(II,II) carboxylates, that do not undergo 1-electron oxidation under the reaction conditions, moderate yields of aziridination products were obtained with very low catalyst loadings. Catalytic systems (e.g., CuI) that work well for aminobromination (>90% yield) using NBS and p-TsNH2 (Thakur, V. V. et al. (2003) "TRANSITION METAL-CATALYZED REGIO- AND STEREOSELECTIVE AMINOBROMINATION OF OLEFINS WITH TsNH2 AND NBS AS NITROGEN AND BROMINE SOURCES," Org. Lett. 5(6):861-864) appear to be unable to tolerate the addition of a base. Catalysts that would be considered stronger Lewis Acids (but not redox active) (e.g., $Rh_2(OAc)_4$) have difficulty catalyzing this process. The results obtained with $Rh_2(cap)_4$Cl show that a dirhodium(II, III)[5+] caprolactame with a strong axial ligand (relative to Br) demonstrate diminished catalytic capacity. Of all the catalysts examined, $Rh_2(cap)_4$ was the most effective.

In addition to the proposed Lewis-acid activation, another mechanistic scenario that may be operative in light of the observed substrate reactivity was examined. Due to the known nucleophilicity of Chloramine-T analogs such as 6, as well as the "through dirhodium" displacement of a halide (for displacement reactions of $Rh_2$-halides see: Bear, J. L. et al. (2001) "SYNTHESIS, ELECTROCHEMISTRY, AND SPECTROSCOPIC CHARACTERIZATION OF BIS-DIRHODIUM COMPLEXES LINKED BY AXIAL LIGANDS," Inorg. Chem. 40(10):2275-2281), another possible route for the formation of 13 (see, Scheme 8). Displacement of bromine from 1 by 6 would give 13 as a metal-bound bromine atom-transfer source.

Scheme 8

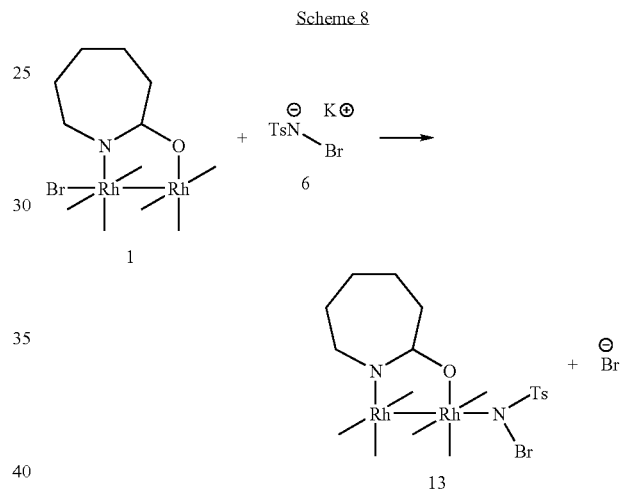

Silver(I) titration experiments identified the presence of chloride ion when 1 was treated with Chloramine-T. A silver (I) halide test was performed to detect Br— as the displacement product of 1 and 6. Treatment of 1 with $Ag(I)BF_4$ does not yield a precipitate. Treatment of NBS with Chloramine-T in the absence of 1 with $Ag(I)BF_4$ does not yield a precipitate. However, in the presence of Chloramine-T, 1 immediately reacts with $Ag(I)BF_4$ to give a white precipitate determined to be AgCl by its solubility in ammonium hydroxide.

In addition, the stoichiometric reaction of 1 with Chloramine-T (2 equiv) and styrene in the absence of potassium carbonate rapidly gave both aminobromination and aziridination products, consistent with the intermediate formation of 13. Furthermore, bromine atom-transfer from 13 would be a sterically demanding process (as both 1-methylcyclohexene and α-methylstyrene were unreactive).

Thus, the present invention relates to a catalyst that mediates an olefin aziridination reaction through the formation of an intermediate having the structures (VI) or (VI):

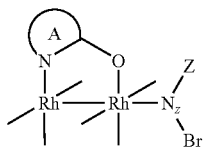

(VI)

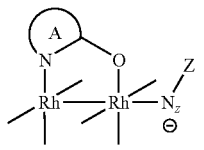

(VII)

wherein A is a ring structure that may be substituted or unsubstituted, $N_z$ is nitrogen and Z is an optionally substituted aryl moiety that increases the electophilicity of Nz. A preferred group Z is p-tolunesulfonamide. The intermediate is preferably formed by reacting a mixed-valent dirhodium(II,III) catalyst ($Rh_2^{5+}$) having the structure (VIII):

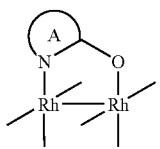

(VIII)

in the presence of an olefin, p-toluenesulfonamide (TsNH2), N bromo-succinimide (NBS), and potassium carbonate.

Figure 3:
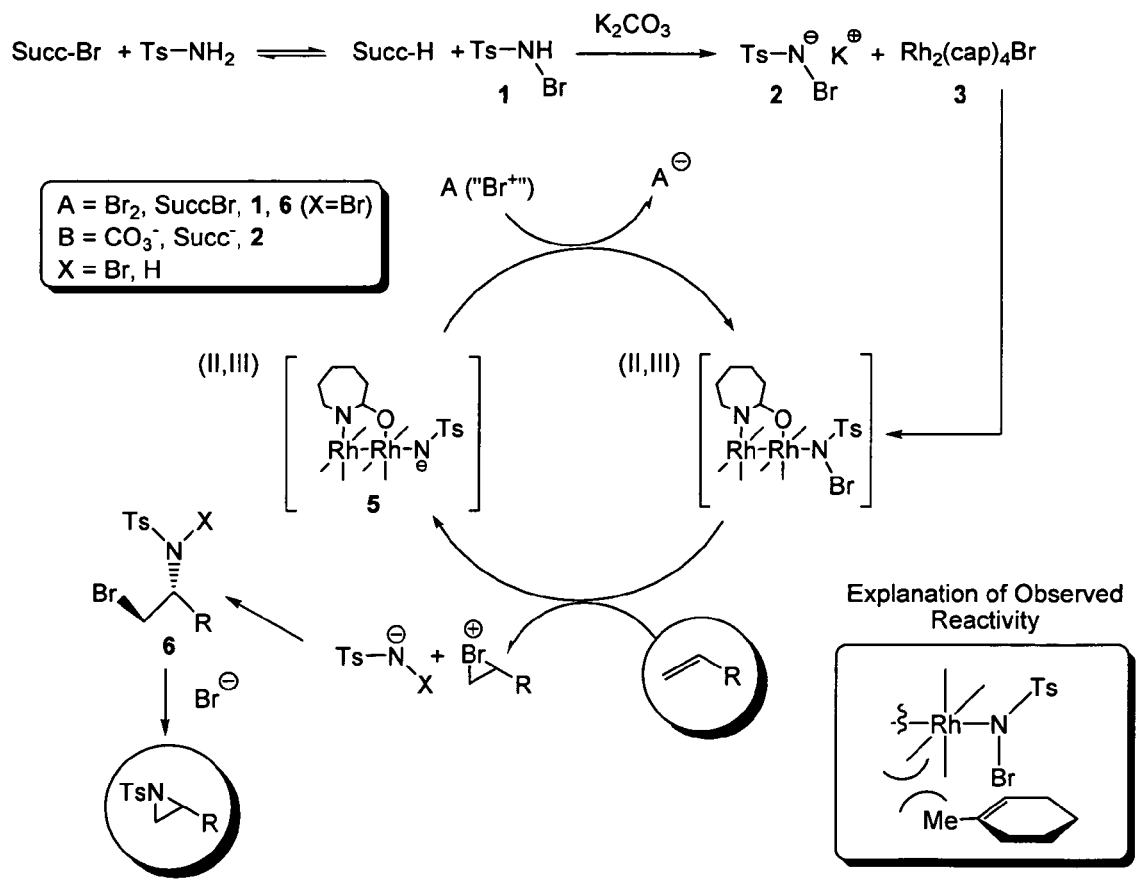
FIG. 3 shows a reaction mechanism for the aziridination reaction using Rh$_2$(cap)$_4$ catalysts of the present invention.

In summary, a catalytic olefin aziridination protocol has been developed using a multi-valent dirhodium catalyst. A selection of olefins has been converted to aziridines in moderate to high yields under extremely mild conditions with as little as 0.01 mol % catalyst. Without limitation to the present invention, a mechanism has been advanced that suggests that dirhodium(II,III) caprolactamate operates as a Lewis-acid catalyst (i.e., facilitating a radical chain process to generate an electropositive bromine source, and mediating a subsequent Lewis-acid assisted bromonium ion formation) and is capable of generating other potentially useful intermediates. The mechanism is illustrated in FIG. 3, and below:

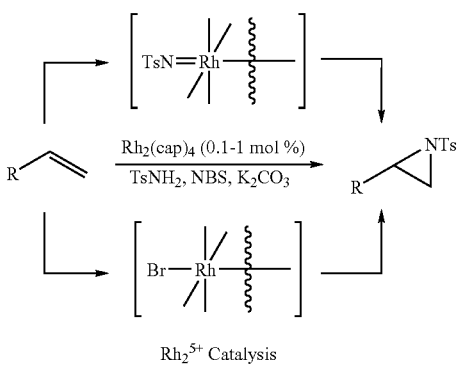

The use of dirhodium(II,III) carboxamidates as redox catalysts for the aziridination of olefins is unprecedented and represents a novel application of the carboxamidate class of catalysts. Unlike dirhodium carboxylates, dirhodium(II,III) carboxamidates do not make use of nitrenes to effect aziridination (Müller, P. et al. (1996) "A METHOD FOR RHODIUM(II)-CATALYZED AZIRIDINATION OF OLEFINS," Tetrahedron 52:1543; Müller, P. et al. (1998) "THE RHODIUM(II)-CATALYZED AZIRIDINATION OF OLEFINS WITH\{[(4-NITROPHENYL)SULFONYL] IMINO\}PHENYL-BOLD LAMBDA 3-IODANE," Can. J. Chem. 76:738-750; Guthikonda, K. et al. (2002) "A UNIQUE AND HIGHLY EFFICIENT METHOD FOR CATALYTIC OLEFIN AZIRIDINATION," J. Am. Chem. Soc. 124:13672; Liang, J.-L. et al. (2002) "RHODIUM(II,II) DIMER AS AN EFFICIENT CATALYST FOR AZIRIDINATION OF SULFONAMIDES AND AMIDATION OF STEROIDS," Org. Lett. 4:4507; Liang, J. L. et al. (2003) "CHIRAL RHODIUM(II,II) DIMERS CATALYZED ENANTIOSELECTIVE INTRAMOLECULAR AZIRIDINATION OF SULFONAMIDES AND CARBAMATES," Tetrahedron Lett. 44:5917; Fruit, C. et al. (2004) "ASYMMETRIC TRANSFER OF NITRENES CATALYZED BY CHIRAL DIRHODIUM(II) USING AROMATIC SULFAMATE ESTERS," Tetrahedron-Asymmetry 15:1019; see also Levites-Agababa, E. et al. (2002) "AMIDOGLYCOSYLATION VIA METAL-CATALYZED INTERNAL NITROGEN ATOM DELIVERY," Org. Lett. 4(5):863-865; Padwa, A. et al. (2002) "STEREOCHEMICAL ASPECTS OF THE IODINE(III)-MEDIATED AZIRIDINATION REACTION OF SOME CYCLIC ALLYLIC CARBAMATES," Org. Lett. 4(13):2137-2139; Padwa, A. et al. (2004) "RHODIUM(II)-CATALYZED AZIRIDINATION OF ALLYL-SUBSTITUTED SULFONAMIDES AND CARBAMATES," J. Org. Chem. 69(19):6377-6386), rather the catalyst plays a multifunctional role. The redox activity of dirhodium (II,III) carboxamidates generates an electropositive source of bromine in situ from N-bromosuccinimide (NBS) and p-tosylsulfonamide (TsNH2) while acting as a Lewis acid to activate the bromine source (FIG. 3). Unlike the Sharpless azirdination method (Jeong, J. U. et al. (1998) "BROMINE-CATALYZED AZIRIDINATION OF OLEFINS. A RARE EXAMPLE OF ATOM-TRANSFER REDOX CATALYSIS BY A MAIN GROUP ELEMENT," J. Am. Chem. Soc. 1998, 120(27): 6844-6845; Ali, S. I. et al. (1999) "PYRIDINIUM HYDROBROMIDE PERBROMIDE: A VERSATILE CATALYST FOR AZIRIDINATION OF OLEFINS USING CHLORAMINE-T," Org. Lett. 1(5); 705-707; Dauban, P. et al. (2001) "INTRAMOLECULAR BROMINE-CATALYZED AZIRIDINATION: A NEW DIRECT ACCESS TO CYCLIC SULFONAMIDES," Tetrahedron Lett. 42:1037-1040; Thakur, V. V. et al. (2003) "N-BROMOAMIDES AS VERSATILE CATALYSTS FOR AZIRIDINATION OF OLEFINS USING CHLORAMINE-T," Tetrahedron Lett. 44:989-992; Jain, S. L. et al. (2004) "AN EFFICIENT TRANSITION METAL-FREE AZIRIDINATION OF ALKENES WITH CHLORAMINE-T USING AQUEOUS $H_2O_2$/HBR," Tetrahedron Lett. 45:8731-

8732). The catalyst of the present invention obviates the need to use a strong base (e.g., Chloramine-T) and avoids the undesired 1,2 dibromide products generated by the use of phenyltrimethylammonium tribromide (PTAB).

Specific advantages of dirhodium(II,III) carboxamidate catalyzed aziridinations include the ability to avoid the unproductive C—H insertion pathways that are associated with nitrenes and the harsh reaction conditions of Chloramine-T while maintaining the level of selectivity observed with those chemistries. The catalysts of the present invention have a remarkable advantage in their efficiency and simplicity. For example, dirhodium(II,II) caprolactamate can be used in as little as 0.01 mol % to achieve the aziridination of an olefin (e.g., 4-methylstyrene with NBS and TSNH2.

Having now generally described the invention, the same will be more readily understood through reference to the following examples, which are provided by way of illustration, and are not intended to be limiting of the present invention, unless specified.

EXAMPLE 1

Efficient Aziridination of Olefins Catalyzed by Mixed Valent Dirhodium(II,III) Caprolactamate General. All reagents were commercially obtained unless otherwise noted. Yields reported are for isolated yields. All products were characterized and in agreement with those previously reported (see, Evans, D. A. et al. (1994) "DEVELOPMENT OF THE COPPER-CATALYZED OLEFIN AZIRIDINATION REACTION," "J. Am. Chem. Soc. 116:2742-2753; Jeong, J. U. et al. (1998) "BROMINE-CATALYZED AZIRIDINATION OF OLEFINS. A RARE EXAMPLE OF ATOM-TRANSFER REDOX CATALYSIS BY A MAIN GROUP ELEMENT," J. Am. Chem. Soc. 1998, 120(27): 6844-6845; Cui, Y. et al. (2003) "EFFICIENT AZIRIDINATION OF OLEFINS CATALYZED BY A UNIQUE DISILVER(I) COMPOUND," J. Am. Chem. Soc. 125 (52):16202-16203; Dauban, P. et al. (2000) "SYNTHRESIS OF CYCLIC SULFONAMIDES VIA INTRAMOLECULAR COPPER-CATALYZED REACTION OF UNSATURATED IMINOIODINANES," Org. Lett. 2(15): 2327-2329).

NBS was recrystallized from water according to the guidelines of Armarego and Chai (Armarego, W. L. F. and Chai, C. L. L. (2003) In: *Purification of Laboratory Chemicals; 5th* ed., Elsevier Science: New York. p-TsNH$_2$ and K$_2$CO$_3$ (anhydrous, granular) were used as received. Olefins (except Entries 10 and 11, Table 1) were filtered over a plug of alumina and distilled prior to use. Trans-2-phenyl-1-vinylcyclopropane 9 was prepared according the procedure of Fu, et al. (1991) ("MECHANISTIC STUDY OF A SYNTHETICALLY USEFUL MONOOXYGENASE MODEL USING THE HYPERSENSITIVE PROBE TRANS-2-PHENYL-1-VINYLCYCLOPROPANE," J. Org. Chem. 56(23):6497-6500). Sulfamate indan-2-yl ester 7 was prepared according to the procedure of Espino, et al. (2001) ("Synthesis of 1,3-Difunctionalized Amine Derivatives through Selective C—H Bond Oxidation," J. Am. Chem. Soc. 123(28):6935-6936) 2-Vinylbenzenesulfonamide (Entry 10, Table 1) and 2-allylbenzenesulfonamide (Entry 11, Table 1) were prepared according the procedure of Dauban and Dodd (Dauban, P. et al. (2000) "SYNTHESIS OF CYCLIC SULFONAMIDES VIA INTRAMOLECULAR COPPER-CATALYZED REACTION OF UNSATURATED IMINOIODINANES," Org. Lett. 2(15):2327-2329). Dirhodium(II,II) caprolactamate [Rh$_2$(cap)$_4$.2CH$_3$CN] was prepared as previously described (Doyle, M. P. et al. (1993) "ELECTRONIC AND STERIC CONTROL IN CARBON-HYDROGEN INSERTION REACTIONS OF DIAZZOACETOACETATES CATALYZED BY DIRHODIUM(II) CARBPXYLATES AND CARBOXAMIDES," J. Am. Chem. Soc. 115(3):958-964). $^1$H NMR (400 MHz) and $^{13}$C NMR (100 MHz) spectra were obtained on a Bruker DRX-400 NMR as solutions in CDCl$_3$. Chemical shifts are reported in parts per million (ppm, δ) downfield from Me$_4$Si (TMS); coupling constants are reported in Hertz (Hz). UV-Visible spectra were obtained on a Varian Cary 50 spectrophotometer using a xenon flash lamp. Preparative chromatographic purification was performed using SiliCycle (60 Å, 40-63 mesh) silica gel according to the method of Still, W. C. et al. (1978) ("RAPID CHROMATOGRAPHIC TECHNIQUE FOR PREPARATIVE SEPARATIONS WITH MODERATE RESOLUTION," J. Org. Chem. 43(14):2923-2925). Thin layer chromatography (TLC) was performed on Merck 0.25 mm silica gel 60 F$_{254}$ plates with visualization by fluorescence quenching or aqueous KMnO$_4$ stain. Anhydrous CH$_2$Cl$_2$ was purified prior to use by nitrogen forced-flow over activated alumina as described by Pangbom, A. B. et al. (1996) ("SAFE AND CONVENIENT PROCEDURE FOR SOLVENT PURIFICATION," Organometallics 15(5): 1518-1520).

Representative Procedure for Aziridination: A 25 mL flask equipped with a stirbar was charged with olefin (2.72 mmol, 100 mol %), CH$_2$Cl$_2$ (10 mL), TsNH$_2$ (2.99 mmol, 110 mol %), K$_2$CO$_3$ (5.71 mmol, 210 mol %), and Rh$_2$(cap)$_4$ (0.0027 mmol, 0.1 mol %). To the mixture was added NBS (2.99 mmol, 110 mol %) in one portion to which the color of the solution immediately turned from light blue to red. The flask was sealed with a septum allowing inclusion of air. After twelve hours, silica gel was added to the reaction mixture and the solvent was evaporated. Column chromatography yielded the analytically pure compound.

EXAMPLE 2

NMR Experiments

Control Experiment: NMR analysis was performed 29 minutes after addition of 0.5 mL (0.152 mmol) of a 3.03×10$^{-1}$ M solution of p-toluenesulfonarnide in d-DCM to 0.5 mL (0.149 mmol) of a 2.98×10$^{-1}$ M solution of N-bromosuccinimide. N-bromo-p-toluenesulfonamide was observed as the product in this equilibrium mixture. Data: $^1$H NMR (400 MHz) δ 7.81-7.83 (d, J=8.0 Hz, 2H), 7.40-7.38 (d, J=8.0 Hz, 2H), 5.95 (s, 1H), 2.46 (s, 3H); at 29 minutes: CH$_{3(TsNH2)}$:CH$_{3(TsNHBr)}$=2.7:1.0; at 20 hours: CH$_{3(TsNH2)}$:CH$_{3(TsNHBr)}$= 2.9:1.0. Addition of 100 μL of D$_2$O exchanged protons in the δ 5.95 (s, 1H, —SO$_2$BrN—H) and 5.08 (s, 2H, —SO$_2$NH$_2$) as indicated by loss of signal.

Equilibrium Experiment: A series of 100 μL aliquots of a succinimide solution (1.52×10$^{-1}$ M in d-dichloromethane) was added to an NMR tube with N-bromosuccinimide (1.5× 10$^{-1}$ mmol) and p-toluenesulfonarnide (1.5×10$^{-1}$ mmol) in 1 mL of d-dichloromethane. The ratio of —CH$_3$ substituents is shown in Table 2.

TABLE 2

| Sample | CH$_{3(TsNH2)}$:CH$_{3(TsNHBr)}$ |
| --- | --- |
| Initial | 2.0:1.0 |
| 100 uL succinimide solution | 3.0:1.0 |
| 200 uL succinimide solution | 4.3:1.0 |
| 300 uL succinimide solution | 6.0:1.0 |
| 400 uL succinimide solution | 6.0:1.0 |
| 900 uL succinimide solution | 12.0:1.0 |

Characterization of Basified Salt: A solution of N-bromosuccinimide (2.75×10$^{-1}$ mmol) and p-toluenesulfonamide (2.75×10$^{-1}$ mmol) in 1 mL of d-chloroform was placed in an NMR tube. A control spectrum indicated the previously observed equilibrium had been established. Anhydrous potassium carbonate (76 mg) was added. A yellow precipitate formed above the potassium carbonate. The relative ratios from the $^1$H NMR (400 MHz) spectra are shown in Table 3.

TABLE 3

| Compounds | Ratio |
|---|---|
| $CH_{3(TsNH2)}:CH_{3(TsNHBr)}$ | 1.0:0.0[a] |
| $CH_{2(NBS)}:CH_{2(succinimide)}$ | 1.0:1.5 |
| $NBS:TsNH_2$ | 1.1:1.0 |
| $TsNH_2:Succinimide$ | 1.0:1.4 |

[a]TsNHBr was not observed

Isolation of Salt: A solution of N-bromosuccinimide ($2.75\times10^{-1}$ mmol) and p-toluenesulfonamide ($2.75\times10^{-1}$ mmol) in 1 mL of dichloromethane was placed in a vial. Anhydrous potassium carbonate (76 mg) was added and a yellow precipitate formed. The precipitate was filtered and dried in vacuo. The yellow powder (10 mg) was placed in an NMR tube and dissolved with $d_6$-dimethylsulfoxide. The relative ratios from the $^1$H NMR (400 MHz) spectra are as follows: $CH_{3(TsNH2)}:CH_{3(TsNHBr)}$=3.0:1.0—Signals of TsNBr$^-$ were shifted upfield from TsNH$_2$ as expected for the anion. Potassium N-bromo-p-toluenesulfonamide was only observed product in an equilibrium mixture. $^1$H NMR in DMSO (400 MHz) δ 7.58-7.56 (d, J=8.0 Hz, 2H), 7.27-7.25 (d, J=8.0 Hz, 2H), 2.31 (s, 3H).

(2-(4-Methylphenyl)-2-(N-bromo-p-toluene-sulfonamino)-1-bromo-ethane, 12: 12 (10 mg, $2.2\times10^{-2}$ mmol) was placed in an NMR tube and diluted with 1 mL of d-dichloromethane. Succinimide (3 mg, $3.0\times10^{-2}$ mmol) was added giving N-bromosuccinimide and aminobromide 3 as observed by $^1$H NMR. Relative ratios are shown in Table 4.

TABLE 4

| Compounds | Ratio |
|---|---|
| $CH_{2(NBS)}:CH_{2(succinimide)}$ | 1.0:7.1 |
| $CH_{2(NBS)}:CH_{3(N-bromo-aminobromide)}$ | 1.0:5.4 |
| $CH_{3(aminobromide)}:CH_{3(N-bromo-aminobromide)}$ | 1.0:5.3 |
| $CH_{2(succinimide)}:CH_{3(N-bromo-aminobromide)}$ | 1.3:1.0 |

Compound 2 was prepared as follows: to a solution of Rh$_2$(cap)$_4$ (0.014 mmol, 100 mol %) in 5 mL CH$_2$Cl$_2$ was added N-chlorosuccinimide (0.020 mmol, 140 mol %) to which the color of the solution turned from light blue to red. After 1 hr, 1 mL of MeOH was added. The solution was passed through a short plug of silica gel and evaporated yielding a red solid (6:1 CH$_2$Cl$_2$/MeOH, TLC R$_f$=0.40). Crystals were obtained by slow evaporation from MeOH/hexanes (1:50). C$_{27}$H$_{51}$Cl$_1$N$_4$O$_7$Rh$_2$, M=784.99, monoclinic, space group P2$_1$, α=8.3834(5) Å, b=18.8291 (11) Å, c=10.2686(6) Å, β=98.088(1), U=1604.8(2) Å3, Z=2, T=173 K, MoKα (0.71073 Å), 25387 reflection measured, 7344 unique (R$_{int}$=0.0318), which were all used in calculations. The final wR2 was 0.0623 (all data). The structure of compound 2 is shown below, and in FIGS. 1A, 1B and 1C.

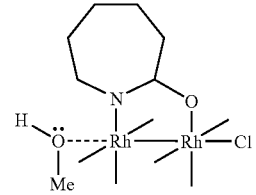

2

The compound:

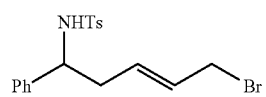

was purified by chromatography on silica gel (4:1 hexanes/EtOAc). Purification gave a clear oil: TLC R$_f$=0.22 (5:1 hexanes/EtOAc); $^1$H NMR (400 MHz) δ 7.58 (d, J=8.0 Hz, 2H), 7.20-7.15 (m, 5H), 7.08-7.04 (m, 2H), 5.66 (dt, J=15.2, 7.6 Hz, 1H), 5.42 (dt, J=14.8, 7.2 Hz, 1H), 5.10 (d, J=7.2 Hz, 1H), 4.35 (q, J=7.2 Hz, 1H), 3.78 (d, J=7.6, 2H), 2.53-2.43 (m, 2H), 2.38 (s, 3H); $^{13}$C-NMR (100 MHz) δ 143.2, 140.0, 137.4, 130.5, 130.2, 129.4, 128.5, 127.5, 127.1, 126.4, 57.3, 39.9, 32.2, 21.5; HRMS (FAB) calculated for C$_{18}$H$_{21}$BrNO$_2$S 394.0476, found 394.0463 (M+H)$^+$.

EXAMPLE 3

X-Ray Data

In order to determine the x-ray crystallographic structure of compound 2, a reddish-orange plate with approximate orthogonal dimensions 0.306×0.124×0.018 mm$^3$ was placed and optically centered on the Bruker SMART CCD system at −100° C. The initial unit cell was indexed using a least-squares analysis of a random set of reflections collected from three series of 0.3° wide ω-scans, 10 seconds per frame, and 25 frames per series that were well distributed in reciprocal space. Data frames were collected [MoKα] with 0.3° wide ω-scans, 40 seconds per frame and 606 frames per series. Five complete series were collected at varying Φ angles (Φ=0°, 72°, 144°, 216°, 288°). The crystal to detector distance was 4.893 cm, thus providing a nearly complete sphere of data to 2θ$_{max}$=55.1320 . A total of 25,387 reflections were collected and corrected for Lorentz and polarization effects and absorption using Blessing's method as incorporated into the program SADABS (Blessing, R. H. (1995) "An Empirical Correction for Absorption Anisotropy," Acta Cryst. A51:33-38; Sheldrick, G. M. (1996) SADABS "Siemens Area Detector Absorption Correction" Universität Göttingen: Göttingen, Germany) with 7,378 unique reflections.

Structural Determination and Refinement: All crystallographic calculations were performed on a Personal computer (PC) with a Pentium 1.80 GHz processor and 512 MB of extended memory. The SHELXTL program package (Sheldrick, G. M. (1994) SHELXTL/PC. Version 5.03; Siemens Analytical X-ray Instruments Inc., Madison, Wis., USA) was implemented to determine the probable space group and set up the initial files. System symmetry, systematic absences and intensity statistics indicated the unique chiral monoclinic space group P2$_1$ (no. 4). The structure was determined by direct methods with the successful location of all the non-hydrogen atoms using the program XS (Sheldrick, G. M., (1990) "Phase Annealing in SHELX-90: Direct Methods for Larger Structures," Acta Cryst. A46:467-473). The structure was refined with XL (Sheldrick, G. M. (1993) Shelxl93 Program for the Refinement of Crystal Structures; University of Göttingen, Germany). The 25,387 data collected were merged during least-squares refinement to 7,344 unique data [R(int)=0.0318]. Multiple least-squares difference-Fourier cycles were required to locate the remaining non-hydrogen atoms. All non-hydrogen atoms were refined anisotropically. Hydrogen atoms were allowed to refine freely (xyzU) but for those attached to the methanol oxygen atoms (U only). The final structure was refined to convergence [$\Delta/\sigma \leq 0.001$] with R(F)=5.91%, wR($F^2$)=11.59%, GOF=1.048 for all 12386 unique reflections [R(F)=4.20%, wR($F^2$)=10.62% for those 9858 data with Fo>4σ(Fo)]. The final difference-Fourier map was featureless indicating that the structure is both correct and complete. The absolute structure parameter, Flack(x) (Flack, H. D. (1983) "On Enantiomorph-Polarity Estimation," Acta Cryst. A39:876-881), was refined and found to be 0.26(2) indicating racemic twinning that was also refined. The function minimized during the full-matrix least-squares refinement was $\Sigma w(Fo^2-Fc^2)$ where w=1/[$\sigma^2(Fo^2)$+$(0.0382*P)^2+0.0*P$] and P=(max($Fo^2$,0)+2*$Fc^2$)/3. An empirical correction for extinction was also attempted but found to be negative and therefore not applied.

The crystal data and structure refinement for [$C_{25}H_{43}N_4O_5ClRh_2$][$CH_3OH$]$_2$ is summarized in Table 5.

TABLE 5

Crystal Data And Structure Refinement For [$C_{25}H_{43}N_4O_5ClRh_2$][$CH_3OH$]$_2$

| Attribute | Value |
|---|---|
| Identification Code | 1071ff |
| Empirical Formula | C27 H51 Cl N4 O7 Rh2 |
| Formula Weight | 784.99 |
| Temperature | 173(2) K |
| Wavelength | 0.71073 Å |
| Crystal System | Monoclinic |
| Space Group | P2(1) |
| Unit Cell Dimensions | a = 8.3834(5) Å  α = 90° |
|  | b = 18.8291(11) Å  β = 98.0880(10)° |
|  | c = 10.2686(6) Å  γ = 90°. |
| Volume | 1604.79(16) Å3 |
| Z | 2 |
| Density (Calculated) | 1.625 Mg/m3 |
| Absorption Coefficient | 1.160 mm − 1 |
| F(000) | 808 |
| Crystal Size | 0.31 × 0.12 × 0.02 mm3 |
| Theta Range For Data Collection | 2.16 to 27.50°. |
| Index Ranges | −10 <= h <= 10, −24 <= k <= 24, |
|  | −13 <= l <= 13 |
| Reflections Collected | 25387 |
| Independent Reflections | 7344 [R(int) = 0.0318] |
| Completeness To Theta = 27.50° | 99.9% |
| Absorption Correction | Empirical, SADABS (multi-scan) |
| Max. And Min. Transmission | 0.9794 and 0.7179 |
| Refinement Method | Full-matrix least-squares on F2 |
| Data/Restraints/Parameters | 7344/1/571 |
| Goodness-Of-Fit On F2 | 1.029 |
| Final R Indices [I > 2sigma(I)] | R1 = 0.0267, |
|  | wR2 = 0.0597 [6732 Data] |
| R Indices (All Data) | R1 = 0.0334, wR2 = 0.0623 |
| Absolute Structure Parameter | 0.26(2) |
| Largest Diff. Peak And Hole | 0.912 and −0.721 e · Å−3 |

The atomic coordinates ($\times 10^4$) and equivalent isotropic displacement parameters ($Å^2 \times 10^3$) for the atoms of compound 2 [$C_{25}H_{43}N_4O_5ClRh_2$][$CH_3OH$]$_2$ are shown in Table 6. U(eq) is defined as one third of the trace of the orthogonalized $U^{ij}$ tensor.

TABLE 6

Atomic Coordinates ($\times 10^4$) And Equivalent Isotropic Displacement Parameters ($Å^2 \times 10^3$) For The Atoms Of Compound 2 [$C_{25}H_{43}N_4O_5ClRh_2$][$CH_3OH$]$_2$

| Atom | x | y | z | U(eq) |
|---|---|---|---|---|
| Rh(1) | 7771(1) | 1436(1) | 3732(1) | 20(1) |
| Rh(2) | 8801(1) | 313(1) | 3098(1) | 19(1) |
| Cl(1) | 6354(1) | 2524(1) | 4603(1) | 34(1) |
| C(1) | 8873(4) | 1421(2) | 1169(3) | 22(1) |
| N(1) | 8238(3) | 1826(2) | 1996(3) | 22(1) |
| O(1) | 9275(3) | 770(1) | 1411(2) | 24(1) |
| C(2) | 9120(5) | 1679(2) | −191(4) | 29(1) |
| C(3) | 7522(5) | 1769(2) | −1097(4) | 35(1) |
| C(4) | 6670(5) | 2461(2) | −877(4) | 37(1) |
| C(5) | 6263(5) | 2566(2) | 504(4) | 37(1) |
| C(6) | 7709(5) | 2553(2) | 1594(4) | 31(1) |
| C(7) | 5377(4) | 543(2) | 2254(3) | 21(1) |
| N(7) | 6556(3) | 82(2) | 2256(3) | 21(1) |
| O(7) | 5571(3) | 1149(1) | 2833(2) | 24(1) |
| C(8) | 3703(4) | 403(2) | 1543(4) | 28(1) |
| C(9) | 3637(5) | 389(3) | 51(4) | 35(1) |
| C(10) | 4232(5) | −296(3) | −498(4) | 37(1) |
| C(11) | 5958(5) | −506(3) | 60(4) | 33(1) |
| C(12) | 6236(5) | −596(2) | 1554(4) | 25(1) |
| C(13) | 7700(4) | 322(2) | 5650(3) | 22(1) |
| N(13) | 8340(3) | −82(2) | 4810(3) | 22(1) |
| O(13) | 7288(3) | 974(1) | 5396(2) | 24(1) |
| C(14) | 7497(4) | 64(2) | 7003(3) | 25(1) |
| C(15) | 9148(5) | 12(2) | 7860(4) | 29(1) |
| C(16) | 10014(5) | −681(2) | 7654(4) | 33(1) |
| C(17) | 10385(5) | −799(2) | 6265(4) | 31(1) |
| C(18) | 8883(5) | −801(2) | 5224(4) | 26(1) |
| C(19) | 11220(4) | 1208(2) | 4524(3) | 23(1) |
| N(19) | 10039(3) | 1659(2) | 4565(3) | 22(1) |
| O(19) | 11017(3) | 598(1) | 3948(2) | 25(1) |
| C(20) | 12927(4) | 1364(2) | 5153(4) | 30(1) |
| C(21) | 13109(5) | 1391(3) | 6669(4) | 40(1) |
| C(22) | 12539(6) | 2092(3) | 7195(5) | 45(1) |
| C(23) | 10801(5) | 2278(3) | 6722(4) | 40(1) |
| C(24) | 10400(5) | 2348(2) | 5237(4) | 30(1) |
| C(25) | 10265(5) | −843(3) | 1143(4) | 34(1) |
| O(25) | 10052(3) | −725(1) | 2475(2) | 24(1) |
| C(31) | 2606(6) | 2597(3) | 2061(6) | 49(1) |
| O(31) | 3470(4) | 3166(2) | 2666(4) | 62(1) |
| C(41) | 4051(5) | −687(3) | 4596(5) | 41(1) |
| O(41) | 2926(3) | −1113(2) | 3758(3) | 40(1) |

The bond lengths [Å] for [$C_{25}H_{43}N_4O_5ClRh_2$][$CH_3OH$]$_2$ are presented in Table 7.

TABLE 7

Bond Lengths in Å Between The Atoms Of Compound 2 [$C_{25}H_{43}N_4O_5ClRh_2$][$CH_3OH$]$_2$

| Atoms | Bond Length |
|---|---|
| Rh(1)—O(13) | 2.008(2) |
| Rh(1)—O(7) | 2.017(2) |
| Rh(1)—N(19) | 2.017(3) |
| Rh(1)—N(1) | 2.017(3) |
| Rh(1)—Rh(2) | 2.4078(3) |
| Rh(1)—Cl(1) | 2.5887(9) |
| Rh(2)—N(13) | 1.996(3) |
| Rh(2)—N(7) | 2.006(3) |
| Rh(2)—O(19) | 2.011(2) |
| Rh(2)—O(1) | 2.023(2) |
| Rh(2)—O(25) | 2.349(2) |
| C(1)—O(1) | 1.286(5) |
| C(1)—N(1) | 1.309(5) |
| C(1)—C(2) | 1.520(5) |
| N(1)—C(6) | 1.480(5) |
| C(2)—C(3) | 1.529(6) |
| C(2)—H(2A) | 0.97(4) |
| C(2)—H(2B) | 0.89(5) |
| C(3)—C(4) | 1.518(7) |

TABLE 7-continued

Bond Lengths in Å Between The Atoms Of Compound 2
[C$_{25}$H$_{43}$N$_4$O$_5$ClRh$_2$][CH$_3$OH]$_2$

| Atoms | Bond Length |
|---|---|
| C(3)—H(3A) | 1.00(4) |
| C(3)—H(3B) | 0.99(4) |
| C(4)—C(5) | 1.517(6) |
| C(4)—H(4A) | 0.94(4) |
| C(4)—H(4B) | 0.91(6) |
| C(5)—C(6) | 1.530(6) |
| C(5)—H(5A) | 0.96(4) |
| C(5)—H(5B) | 1.13(5) |
| C(6)—H(6A) | 0.91(4) |
| C(6)—H(6B) | 1.00(4) |
| C(7)—O(7) | 1.285(4) |
| C(7)—N(7) | 1.316(4) |
| C(7)—C(8) | 1.511(5) |
| N(7)—C(12) | 1.472(4) |
| C(8)—C(9) | 1.525(5) |
| C(8)—H(8A) | 0.96(5) |
| C(8)—H(8B) | 0.98(4) |
| C(9)—C(10) | 1.519(7) |
| C(9)—H(9A) | 0.92(5) |
| C(9)—H(9B) | 0.93(4) |
| C(10)—C(11) | 1.531(6) |
| C(10)—H(10A) | 1.11(4) |
| C(10)—H(10B) | 0.96(5) |
| C(11)—C(12) | 1.529(6) |
| C(11)—H(11A) | 0.98(4) |
| C(11)—H(11B) | 0.97(4) |
| C(12)—H(12A) | 0.94(3) |
| C(12)—H(12B) | 0.94(4) |
| C(13)—O(13) | 1.292(5) |
| C(13)—N(13) | 1.319(4) |
| C(13)—C(14) | 1.504(5) |
| N(13)—C(18) | 1.473(5) |
| C(14)—C(15) | 1.535(5) |
| C(14)—H(14A) | 1.00(4) |
| C(14)—H(14B) | 0.81(4) |
| C(15)—C(16) | 1.522(6) |
| C(15)—H(15A) | 1.10(4) |
| C(15)—H(15B) | 0.84(5) |
| C(16)—C(17) | 1.518(6) |
| C(16)—H(16A) | 0.90(5) |
| C(16)—H(16B) | 1.03(6) |
| C(17)—C(18) | 1.533(5) |
| C(17)—H(17A) | 0.98(4) |
| C(17)—H(17B) | 0.99(4) |
| C(18)—H(18A) | 0.98(4) |
| C(18)—H(18B) | 0.92(4) |
| C(19)—O(19) | 1.293(4) |
| C(19)—N(19) | 1.310(4) |
| C(19)—C(20) | 1.514(5) |
| N(19)—C(24) | 1.481(5) |
| C(20)—C(21) | 1.543(5) |
| C(20)—H(20A) | 1.00(5) |
| C(20)—H(20B) | 0.92(4) |
| C(21)—C(22) | 1.528(7) |
| C(21)—H(21A) | 1.10(5) |
| C(21)—H(21B) | 1.02(4) |
| C(22)—C(23) | 1.511(6) |
| C(22)—H(22A) | 0.95(5) |
| C(22)—H(22B) | 0.94(5) |
| C(23)—C(24) | 1.520(6) |
| C(23)—H(23A) | 0.91(5) |
| C(23)—H(23B) | 0.87(4) |
| C(24)—H(24A) | 0.97(5) |
| C(24)—H(24B) | 1.02(4) |
| C(25)—O(25) | 1.421(4) |
| C(25)—H(25A) | 0.95(6) |
| C(25)—H(25B) | 0.91(5) |
| C(25)—H(25C) | 0.93(4) |
| C(31)—O(31) | 1.391(7) |
| C(31)—H(31A) | 0.84(7) |
| C(31)—H(31B) | 1.04(5) |
| C(31)—H(31C) | 0.89(5) |
| O(31)—H(31) | 0.8400 |
| C(41)—O(41) | 1.429(5) |

TABLE 7-continued

Bond Lengths in Å Between The Atoms Of Compound 2
[C$_{25}$H$_{43}$N$_4$O$_5$ClRh$_2$][CH$_3$OH]$_2$

| Atoms | Bond Length |
|---|---|
| C(41)—H(41A) | 0.93(8) |
| C(41)—H(41B) | 1.02(10) |
| C(41)—H(41C) | 0.98(6) |
| O(41)—H(41) | 0.8400 |

The bond angles [°] for [C$_{25}$H$_{43}$N$_4$O$_5$ClRh$_2$][CH$_3$OH]$_2$ are presented in Table 8.

TABLE 8

Bond Angles in Degrees (°) Between The Atoms Of Compound 2
[C$_{25}$H$_{43}$N$_4$O$_5$ClRh$_2$][CH$_3$OH]$_2$

| Atoms | Bond Angle |
|---|---|
| O(13)—Rh(1)—O(7) | 89.59(10) |
| O(13)—Rh(1)—N(19) | 91.18(11) |
| O(7)—Rh(1)—N(19) | 175.63(11) |
| O(13)—Rh(1)—N(1) | 175.61(12) |
| O(7)—Rh(1)—N(1) | 88.36(11) |
| N(19)—Rh(1)—N(1) | 90.59(11) |
| O(13)—Rh(1)—Rh(2) | 88.43(7) |
| O(7)—Rh(1)—Rh(2) | 88.87(7) |
| N(19)—Rh(1)—Rh(2) | 86.85(8) |
| N(1)—Rh(1)—Rh(2) | 87.64(8) |
| O(13)—Rh(1)—Cl(1) | 83.80(7) |
| O(7)—Rh(1)—Cl(1) | 86.34(7) |
| N(19)—Rh(1)—Cl(1) | 98.01(8) |
| N(1)—Rh(1)—Cl(1) | 99.94(9) |
| Rh(2)—Rh(1)—Cl(1) | 170.90(2) |
| N(13)—Rh(2)—N(7) | 90.73(11) |
| N(13)—Rh(2)—O(19) | 89.90(11) |
| N(7)—Rh(2)—O(19) | 177.06(12) |
| N(13)—Rh(2)—O(1) | 176.67(12) |
| N(7)—Rh(2)—O(1) | 90.50(11) |
| O(19)—Rh(2)—O(1) | 88.72(10) |
| N(13)—Rh(2)—O(25) | 94.54(10) |
| N(7)—Rh(2)—O(25) | 97.45(10) |
| O(19)—Rh(2)—O(25) | 85.36(9) |
| O(1)—Rh(2)—O(25) | 88.37(9) |
| N(13)—Rh(2)—Rh(1) | 88.13(8) |
| N(7)—Rh(2)—Rh(1) | 87.53(8) |
| O(19)—Rh(2)—Rh(1) | 89.62(7) |
| O(1)—Rh(2)—Rh(1) | 88.83(7) |
| O(25)—Rh(2)—Rh(1) | 174.30(6) |
| O(1)—C(1)—N(1) | 123.3(3) |
| O(1)—C(1)—C(2) | 114.6(3) |
| N(1)—C(1)—C(2) | 122.1(3) |
| C(1)—N(1)—C(6) | 119.4(3) |
| C(1)—N(1)—Rh(1) | 120.6(2) |
| C(6)—N(1)—Rh(1) | 119.8(2) |
| C(1)—O(1)—Rh(2) | 119.6(2) |
| C(1)—C(2)—C(3) | 111.9(3) |
| C(1)—C(2)—H(2A) | 103(2) |
| C(3)—C(2)—H(2A) | 111(2) |
| C(1)—C(2)—H(2B) | 106(3) |
| C(3)—C(2)—H(2B) | 113(3) |
| H(2A)—C(2)—H(2B) | 113(4) |
| C(4)—C(3)—C(2) | 113.3(4) |
| C(4)—C(3)—H(3A) | 109(2) |
| C(2)—C(3)—H(3A) | 104(2) |
| C(4)—C(3)—H(3B) | 109(2) |
| C(2)—C(3)—H(3B) | 115(2) |
| H(3A)—C(3)—H(3B) | 107(3) |
| C(5)—C(4)—C(3) | 115.0(4) |
| C(5)—C(4)—H(4A) | 107(2) |
| C(3)—C(4)—H(4A) | 110(2) |
| C(5)—C(4)—H(4B) | 102(3) |
| C(3)—C(4)—H(4B) | 120(4) |
| H(4A)—C(4)—H(4B) | 102(4) |
| C(4)—C(5)—C(6) | 115.0(4) |
| C(4)—C(5)—H(5A) | 114(2) |

TABLE 8-continued

Bond Angles in Degrees (°) Between The Atoms Of Compound 2 [C$_{25}$H$_{43}$N$_4$O$_5$ClRh$_2$][CH$_3$OH]$_2$

| Atoms | Bond Angle |
|---|---|
| C(6)—C(5)—H(5A) | 106(2) |
| C(4)—C(5)—H(5B) | 105(3) |
| C(6)—C(5)—H(5B) | 100(3) |
| H(5A)—C(5)—H(5B) | 117(3) |
| N(1)—C(6)—C(5) | 113.2(3) |
| N(1)—C(6)—H(6A) | 114(3) |
| C(5)—C(6)—H(6A) | 109(3) |
| N(1)—C(6)—H(6B) | 108(2) |
| C(5)—C(6)—H(6B) | 108(2) |
| H(6A)—C(6)—H(6B) | 105(3) |
| O(7)—C(7)—N(7) | 122.6(3) |
| O(7)—C(7)—C(8) | 115.3(3) |
| N(7)—C(7)—C(8) | 122.1(3) |
| C(7)—N(7)—C(12) | 119.2(3) |
| C(7)—N(7)—Rh(2) | 121.1(2) |
| C(12)—N(7)—Rh(2) | 119.7(2) |
| C(7)—O(7)—Rh(1) | 119.9(2) |
| C(7)—C(8)—C(9) | 112.9(3) |
| C(7)—C(8)—H(8A) | 108(3) |
| C(9)—C(8)—H(8A) | 107(3) |
| C(7)—C(8)—H(8B) | 111(2) |
| C(9)—C(8)—H(8B) | 110(2) |
| H(8A)—C(8)—H(8B) | 106(3) |
| C(10)—C(9)—C(8) | 114.9(4) |
| C(10)—C(9)—H(9A) | 114(3) |
| C(8)—C(9)—H(9A) | 108(3) |
| C(10)—C(9)—H(9B) | 101(2) |
| C(8)—C(9)—H(9B) | 120(2) |
| H(9A)—C(9)—H(9B) | 98(4) |
| C(9)—C(10)—C(11) | 115.0(3) |
| C(9)—C(10)—H(10A) | 110(2) |
| C(11)—C(10)—H(10A) | 110(2) |
| C(9)—C(10)—H(10B) | 106(3) |
| C(11)—C(10)—H(10B) | 107(3) |
| H(10A)—C(10)—H(10B) | 109(4) |
| C(12)—C(11)—C(10) | 114.0(3) |
| C(12)—C(11)—H(11A) | 106(3) |
| C(10)—C(11)—H(11A) | 114(2) |
| C(12)—C(11)—H(11B) | 107(3) |
| C(10)—C(11)—H(11B) | 113(3) |
| H(11A)—C(11)—H(11B) | 103(3) |
| N(7)—C(12)—C(11) | 112.7(3) |
| N(7)—C(12)—H(12A) | 110(2) |
| C(11)—C(12)—H(12A) | 109(2) |
| N(7)—C(12)—H(12B) | 105(2) |
| C(11)—C(12)—H(12B) | 115(2) |
| H(12A)—C(12)—H(12B) | 105(3) |
| O(13)—C(13)—N(13) | 122.5(3) |
| O(13)—C(13)—C(14) | 115.6(3) |
| N(13)—C(13)—C(14) | 121.8(3) |
| C(13)—N(13)—C(18) | 118.6(3) |
| C(13)—N(13)—Rh(2) | 120.6(2) |
| C(18)—N(13)—Rh(2) | 120.4(2) |
| C(13)—O(13)—Rh(1) | 120.2(2) |
| C(13)—C(14)—C(15) | 109.9(3) |
| C(13)—C(14)—H(14A) | 113(2) |
| C(15)—C(14)—H(14A) | 112(2) |
| C(13)—C(14)—H(14B) | 109(3) |
| C(15)—C(14)—H(14B) | 107(3) |
| H(14A)—C(14)—H(14B) | 106(3) |
| C(16)—C(15)—C(14) | 112.6(3) |
| C(16)—C(15)—H(15A) | 110.6(17) |
| C(14)—C(15)—H(15A) | 106.2(18) |
| C(16)—C(15)—H(15B) | 110(4) |
| C(14)—C(15)—H(15B) | 107(4) |
| H(15A)—C(15)—H(15B) | 110(4) |
| C(17)—C(16)—C(15) | 114.9(3) |
| C(17)—C(16)—H(16A) | 115(3) |
| C(15)—C(16)—H(16A) | 108(3) |
| C(17)—C(16)—H(16B) | 101(3) |
| H(15)—C(16)—H(16B) | 116(3) |
| H(16A)—C(16)—H(16B) | 101(4) |
| C(16)—C(17)—C(18) | 113.5(3) |
| C(16)—C(17)—H(17A) | 108(2) |
| C(18)—C(17)—H(17A) | 108(2) |
| C(16)—C(17)—H(17B) | 109(3) |
| C(18)—C(17)—H(17B) | 108(3) |
| H(17A)—C(17)—H(17B) | 109(3) |
| N(13)—C(18)—H(17) | 112.9(3) |
| N(13)—C(18)—H(18A) | 103(2) |
| C(17)—C(18)—H(18A) | 118(2) |
| N(13)—C(18)—H(18B) | 109(3) |
| C(17)—C(18)—H(18B) | 109(3) |
| H(18A)—C(18)—H(18B) | 105(4) |
| O(19)—C(19)—N(19) | 122.7(3) |
| O(19)—C(19)—C(20) | 115.0(3) |
| N(19)—C(19)—C(20) | 122.2(3) |
| C(19)—N(19)—C(24) | 118.5(3) |
| C(19)—N(19)—Rh(1) | 121.5(2) |
| C(24)—N(19)—Rh(1) | 120.0(2) |
| C(19)—O(19)—Rh(2) | 119.3(2) |
| C(19)—C(20)—C(21) | 113.0(3) |
| C(19)—C(20)—H(20A) | 108(3) |
| C(21)—C(20)—H(20A) | 109(3) |
| C(19)—C(20)—H(20B) | 105(2) |
| C(21)—C(20)—H(20B) | 108(2) |
| H(20A)—C(20)—H(20B) | 113(3) |
| C(22)—C(21)—C(20) | 113.2(4) |
| C(22)—C(21)—H(21A) | 114(3) |
| C(20)—C(21)—H(21A) | 104(3) |
| C(22)—C(21)—H(21B) | 112(2) |
| C(20)—C(21)—H(21B) | 106(2) |
| H(21A)—C(21)—H(21B) | 107(3) |
| C(23)—C(22)—C(21) | 115.0(4) |
| C(23)—C(22)—H(22A) | 109(3) |
| C(21)—C(22)—H(22A) | 111(3) |
| C(23)—C(22)—H(22B) | 109(3) |
| C(21)—C(22)—H(22B) | 110(3) |
| H(22A)—C(22)—H(22B) | 102(4) |
| C(22)—C(23)—C(24) | 114.2(4) |
| C(22)—C(23)—H(23A) | 110(3) |
| C(24)—C(23)—H(23A) | 110(3) |
| C(22)—C(23)—H(23B) | 107(3) |
| C(24)—C(23)—H(23B) | 117(3) |
| H(23A)—C(23)—H(23B) | 96(4) |
| N(19)—C(24)—C(23) | 113.1(4) |
| N(19)—C(24)—H(24A) | 110(3) |
| C(23)—C(24)—H(24A) | 111(3) |
| N(19)—C(24)—H(24B) | 109(2) |
| C(23)—C(24)—H(24B) | 107(2) |
| H(24A)—C(24)—H(24B) | 105(4) |
| O(25)—C(25)—H(25A) | 106(3) |
| O(25)—C(25)—H(25B) | 113(3) |
| H(25A)—C(25)—H(25B) | 101(4) |
| O(25)—C(25)—H(25C) | 107(3) |
| H(25A)—C(25)—H(25C) | 109(4) |
| H(25B)—C(25)—H(25C) | 120(4) |
| C(25)—O(25)—Rh(2) | 120.9(2) |
| O(31)—C(31)—H(31A) | 121(4) |
| O(31)—C(31)—H(31B) | 109(3) |
| H(31A)—C(31)—H(31B) | 93(5) |
| O(31)—C(31)—H(31C) | 114(3) |
| H(31A)—C(31)—H(31C) | 108(5) |
| H(31B)—C(31)—H(31C) | 109(4) |
| C(31)—O(31)—H(31) | 109.5 |
| O(41)—C(41)—H(41A) | 106(4) |
| O(41)—C(41)—H(41B) | 102(6) |
| H(41A)—C(41)—H(41B) | 121(7) |
| O(41)—C(41)—H(41C) | 112(3) |
| H(41A)—C(41)—H(41C) | 113(5) |
| H(41B)—C(41)—H(41C) | 103(6) |
| C(41)—O(41)—H(41) | 109.5 |

The anisotropic displacement parameters (Å$^2$×10$^3$) for [C$_{25}$H$_{43}$N$_4$O$_5$ClRh$_2$][CH$_3$OH]$_2$ are presented in Table 9. The anisotropic displacement factor exponent takes the form: $-2\pi^2[h^2 a^{*2} U^{11} + \ldots + 2 h k a^* b^* U^{12}]$.

TABLE 9

Anisotropic Displacement Parameters (Å² × 10³) for [C$_{25}$H$_{43}$N$_4$O$_5$ClRh$_2$][CH$_3$OH]$_2$

| Atom | U$^{11}$ | U$^{22}$ | U$^{33}$ | U$^{23}$ | U$^{13}$ | U$^{12}$ |
|---|---|---|---|---|---|---|
| Rh(1) | 18(1) | 21(1) | 19(1) | −1(1) | −2(1) | 0(1) |
| Rh(2) | 18(1) | 21(1) | 17(1) | 0(1) | −1(1) | 1(1) |
| Cl(1) | 30(1) | 28(1) | 42(1) | −9(1) | −2(1) | 4(1) |
| C(1) | 20(1) | 25(2) | 22(2) | 3(2) | 0(1) | −3(2) |
| N(1) | 23(1) | 21(2) | 21(2) | 1(1) | −2(1) | −1(1) |
| O(1) | 26(1) | 26(1) | 21(1) | 3(1) | 4(1) | 1(1) |
| C(2) | 31(2) | 30(2) | 26(2) | 4(2) | 6(2) | −1(2) |
| C(3) | 34(2) | 44(2) | 25(2) | 3(2) | −2(2) | −11(2) |
| C(4) | 35(2) | 37(2) | 33(2) | 9(2) | −9(2) | −7(2) |
| C(5) | 34(2) | 34(2) | 41(2) | 9(2) | −2(2) | 6(2) |
| C(6) | 40(2) | 24(2) | 30(2) | 3(2) | 2(2) | −3(2) |
| C(7) | 21(2) | 24(2) | 19(2) | 2(1) | 1(1) | −3(1) |
| N(7) | 20(1) | 23(2) | 20(1) | −1(1) | −1(1) | −2(1) |
| O(7) | 21(1) | 25(1) | 26(1) | −3(1) | 0(1) | 1(1) |
| C(8) | 18(2) | 32(2) | 33(2) | −5(2) | 0(1) | −3(2) |
| C(9) | 25(2) | 47(3) | 29(2) | 0(2) | −5(1) | −3(2) |
| C(10) | 29(2) | 51(3) | 27(2) | −7(2) | −4(2) | −3(2) |
| C(11) | 24(2) | 49(3) | 27(2) | −13(2) | 1(2) | −4(2) |
| C(12) | 21(2) | 21(2) | 31(2) | −5(2) | 0(2) | −3(2) |
| C(13) | 16(1) | 27(2) | 21(2) | −1(2) | −1(1) | 0(2) |
| N(13) | 24(1) | 23(2) | 18(1) | 0(1) | −2(1) | 0(1) |
| O(13) | 25(1) | 26(1) | 21(1) | −1(1) | 3(1) | 2(1) |
| C(14) | 25(2) | 32(2) | 19(2) | 0(1) | 2(1) | −1(2) |
| C(15) | 37(2) | 35(2) | 14(2) | −1(2) | −1(2) | 0(2) |
| C(16) | 31(2) | 42(2) | 21(2) | 4(2) | −9(2) | 2(2) |
| C(17) | 27(2) | 35(2) | 31(2) | 5(2) | 0(2) | 5(2) |
| C(18) | 32(2) | 24(2) | 22(2) | 1(2) | 1(2) | 5(2) |
| C(19) | 19(2) | 28(2) | 22(2) | 1(1) | 2(1) | −3(1) |
| N(19) | 20(1) | 23(2) | 21(2) | −3(1) | −1(1) | −4(1) |
| O(19) | 20(1) | 26(1) | 26(1) | −3(1) | −3(1) | 1(1) |
| C(20) | 19(2) | 34(2) | 33(2) | −6(2) | −1(1) | 1(2) |
| C(21) | 32(2) | 45(2) | 38(2) | 2(2) | −15(2) | 3(2) |
| C(22) | 38(2) | 65(3) | 29(2) | −15(2) | −8(2) | −5(2) |
| C(23) | 38(2) | 47(3) | 35(2) | −17(2) | 6(2) | −5(2) |
| C(24) | 23(2) | 28(2) | 35(2) | −6(2) | −5(2) | −2(2) |
| C(25) | 34(2) | 40(2) | 28(2) | −4(2) | 5(2) | 7(2) |
| O(25) | 28(1) | 24(1) | 19(1) | −1(1) | −1(1) | 4(1) |
| C(31) | 37(2) | 52(3) | 58(3) | −1(3) | 6(2) | 3(2) |
| O(31) | 50(2) | 54(2) | 74(3) | −8(2) | −17(2) | 19(2) |
| C(41) | 32(2) | 42(3) | 47(3) | 9(2) | −1(2) | −2(2) |
| O(41) | 38(2) | 37(2) | 41(2) | 11(1) | −12(1) | 3(1) |

The hydrogen coordinates (×10⁴) and isotropic displacement parameters (Å²×10³) for [C$_{25}$H$_{43}$N$_4$O$_5$ClRh$_2$][CH$_3$OH]$_2$ are shown in Table 10.

TABLE 10

Hydrogen Coordinates (× 10⁴) And Isotropic Displacement Parameters (Å² × 10³) For The Atoms Of Compound 2 [C$_{25}$H$_{43}$N$_4$O$_5$ClRh$_2$][CH$_3$OH]$_2$

| Atom | x | y | z | U(eq) |
|---|---|---|---|---|
| H(2A) | 9750(40) | 1300(20) | −500(30) | 20(9) |
| H(2B) | 9670(60) | 2080(30) | −60(50) | 45(13) |
| H(3A) | 7830(50) | 1770(20) | −2010(40) | 27(10) |
| H(3B) | 6750(40) | 1380(20) | −1060(30) | 19(8) |
| H(4A) | 7300(50) | 2850(20) | −1060(40) | 19(9) |
| H(4B) | 5710(70) | 2560(30) | −1380(50) | 68(17) |
| H(5A) | 5520(50) | 2230(20) | 760(40) | 22(10) |
| H(5B) | 5900(60) | 3140(30) | 540(50) | 58(15) |
| H(6A) | 8510(50) | 2830(20) | 1350(40) | 25(11) |
| H(6B) | 7380(50) | 2800(20) | 2380(40) | 27(10) |
| H(8A) | 3010(50) | 780(20) | 1750(40) | 32(12) |
| H(8B) | 3250(40) | −38(19) | 1850(30) | 11(8) |
| H(9A) | 2620(60) | 520(20) | −320(40) | 39(12) |
| H(9B) | 4210(50) | 720(20) | −360(40) | 25(10) |
| H(10A) | 4110(50) | −270(20) | −1590(40) | 38(12) |
| H(10B) | 3540(60) | −660(30) | −250(40) | 40(12) |
| H(11A) | 6310(50) | −950(20) | −310(40) | 29(11) |
| H(11B) | 6750(50) | −160(20) | −150(40) | 35(12) |
| H(12A) | 5320(40) | −820(20) | 1810(30) | 11(8) |
| H(12B) | 7100(40) | −890(20) | 1880(40) | 16(9) |
| H(14A) | 6880(40) | −390(20) | 6990(30) | 11(8) |
| H(14B) | 6970(50) | 350(20) | 7340(40) | 20(9) |
| H(15A) | 9850(40) | 469(19) | 7590(30) | 14(9) |
| H(15B) | 8980(50) | 40(30) | 8650(50) | 56(16) |
| H(16A) | 10870(60) | −720(20) | 8290(50) | 39(12) |
| H(16B) | 9410(60) | −1140(30) | 7810(50) | 58(15) |
| H(17A) | 10930(40) | −1260(20) | 6240(30) | 14(8) |
| H(17B) | 11120(50) | −420(20) | 6040(40) | 31(12) |
| H(18A) | 8960(50) | −1040(20) | 4390(40) | 25(10) |
| H(18B) | 8060(50) | −1030(20) | 5560(40) | 32(11) |
| H(20A) | 13260(60) | 1830(30) | 4820(50) | 48(14) |
| H(20B) | 13520(50) | 990(20) | 4920(40) | 20(10) |
| H(21A) | 12440(60) | 920(30) | 6930(50) | 47(13) |
| H(21B) | 14290(50) | 1290(20) | 6990(40) | 27(10) |
| H(22A) | 12710(60) | 2100(30) | 8130(50) | 47(13) |
| H(22B) | 13200(50) | 2460(20) | 6990(40) | 31(11) |
| H(23A) | 10520(60) | 2680(20) | 7120(50) | 43(13) |
| H(23B) | 10210(50) | 1990(20) | 7110(40) | 29(11) |
| H(24A) | 9520(50) | 2680(20) | 5000(40) | 35(12) |
| H(24B) | 11370(50) | 2580(20) | 4900(40) | 34(11) |
| H(25A) | 9340(70) | −1100(30) | 760(50) | 65(16) |
| H(25B) | 11060(60) | −1160(30) | 1060(50) | 58(15) |
| H(25C) | 10270(50) | −400(20) | 740(40) | 32(11) |
| H(31A) | 3050(80) | 2210(40) | 1940(60) | 70(20) |
| H(31B) | 2340(50) | 2690(30) | 1060(50) | 56(15) |
| H(31C) | 1690(60) | 2500(30) | 2380(50) | 46(13) |
| H(31) | 4289 | 3014 | 3152 | 90(20) |
| H(41A) | 3890(80) | −220(40) | 4290(70) | 90(20) |
| H(41B) | 5110(120) | −950(60) | 4540(90) | 170(40) |
| H(41C) | 3920(70) | −740(30) | 5520(60) | 71(17) |
| H(41) | 2943 | −1530 | 4049 | 59(16) |

Table 11 presents the bond lengths (in Å) and the hydrogen bond angles (in degrees (°) for [C$_{25}$H$_{43}$N$_4$O$_5$ClRh$_2$][CH$_3$OH]$_2$.

TABLE 11

Hydrogen Bond Lengths (Å) And Hydrogen Bond angles (°) For The Atoms Of Compound 2 [C$_{25}$H$_{43}$N$_4$O$_5$ClRh$_2$][CH$_3$OH]$_2$

| D—H...A | d(D—H) | d(H...A) | d(D...A) | <(DHA) |
|---|---|---|---|---|
| (31)—H(31)...Cl(1) | 0.84 | 2.31 | 3.149(4) | 173.8 |
| (41)—H(41)...Cl(1)#1 | 0.84 | 2.28 | 3.083(3) | 159.4 |

Symmetry transformations used to generate equivalent atoms:
1 −x + 1, y − 1/2, −z + 1

All publications, patents and patent applications mentioned in this specification are herein incorporated by reference to the same extent as if each individual publication or patent application was specifically and individually indicated to be incorporated by reference While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for producing an aziridine compound, which comprises reacting an olefin with a mixed-valent dirhodium (II,III) catalyst ($Rh_2^{5+}$) under conditions sufficient to convert said olefin into said aziridine compound.

2. The method of claim 1, wherein said mixed-valent dirhodium(II,III) catalyst ($Rh_2^{5+}$) is an analogue or derivative of a member of the carboxamidate class of dirhodium(II,II) paddlewheel complexes.

3. The method of claim 2, wherein the arms of said carboxamidate class of dirhodium(II,II) paddlewheel complexes comprises seven membered rings.

4. The method of claim 3, wherein said mixed-valent dirhodium(II,III) catalyst ($Rh_2^{5+}$) is dirhodium(II,II) caprolactamate [$Rh_2(cap)_4$], or a derivative or analogue thereof.

5. The method of claim 1, wherein said mixed-valent dirhodium(II,III) catalyst ($Rh_2^{5+}$) catalyzes the conversion of said olefin to said aziridine compound via an aminobromination reaction.

6. The method of claim 1, wherein said olefin is reacted with said mixed-valent dirhodium(II,III) catalyst ($Rh_2^{5+}$) in the presence of p-toluenesulfonamide (TsNH2), N bromosuccinimide (NBS), and potassium carbonate.

7. The method of claim 4, wherein said olefin is reacted with said mixed-valent dirhodium(II,III) catalyst ($Rh_2^{5+}$) in the presence of p-toluenesulfonamide (TsNH2), N bromosuccinimide (NBS), and potassium carbonate.

8. The method of claim 5, wherein said olefin is reacted with said mixed-valent dirhodium(II,III) catalyst ($Rh_2^{5+}$) in the presence of p-toluenesulfonamide (TsNH2), N bromosuccinimide (NBS), and potassium carbonate.

9. The method of claim 1, wherein said aziridine compound comprises a structure selected from the group consisting of the structures:

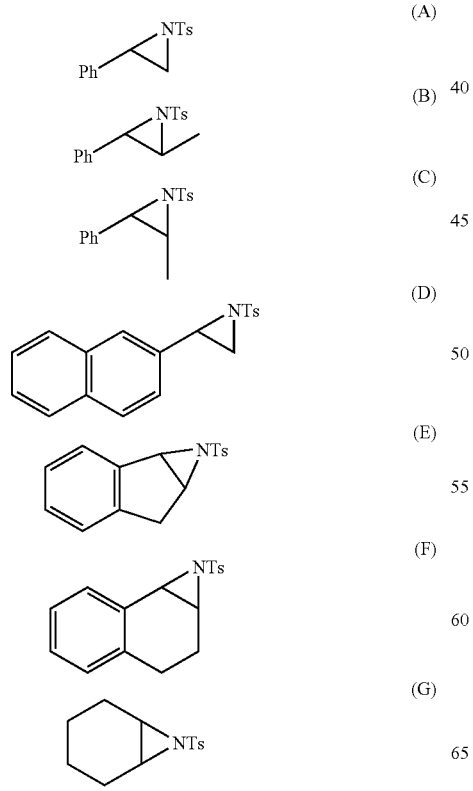

-continued

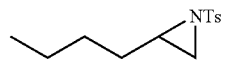

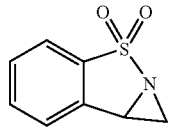

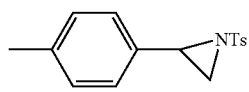

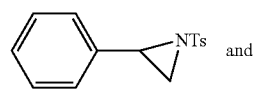

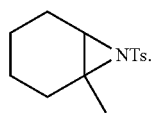

10. The method of claim 7, wherein said aziridine compound comprises a structure selected from the group consisting of the structures:

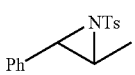

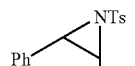

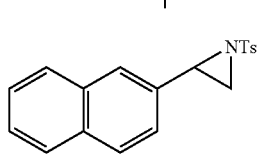

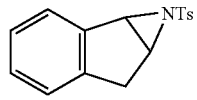

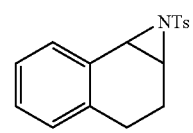

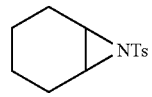

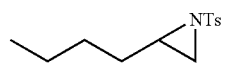

-continued
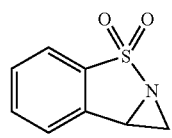 (I)
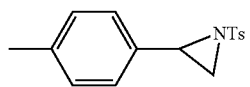 (J)
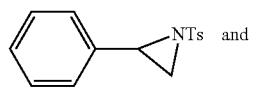 (K) and
 (L)
* * * * *